US007405208B2

(12) United States Patent
Santi et al.

(10) Patent No.: US 7,405,208 B2
(45) Date of Patent: Jul. 29, 2008

(54) BENZOQUINONE ANSAMYCINS

(75) Inventors: Daniel Santi, San Francisco, CA (US); David C. Myles, Kensington, CA (US); Zong-Qiang Tian, Fremont, CA (US); C. Richard Hutchinson, San Mateo, CA (US); Robert Johnson, Lafayette, CA (US); Yi-Qing Zhou, Lafayette, CA (US); Li Feng, Fremont, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 194 days.

(21) Appl. No.: 11/056,470

(22) Filed: Feb. 11, 2005

(65) Prior Publication Data
US 2005/0261263 A1 Nov. 24, 2005

Related U.S. Application Data

(62) Division of application No. 10/212,962, filed on Aug. 5, 2002, now Pat. No. 6,872,715.

(60) Provisional application No. 60/389,225, filed on Jun. 14, 2002, provisional application No. 60/393,929, filed on Jul. 3, 2002, provisional application No. 60/395,275, filed on Jul. 12, 2002, provisional application No. 60/310,779, filed on Aug. 6, 2001.

(51) Int. Cl.
*A61K 31/397* (2006.01)
(52) U.S. Cl. ...................................... 514/183
(58) Field of Classification Search .................. 514/183
See application file for complete search history.

(56) References Cited

U.S. PATENT DOCUMENTS

| 3,595,955 | A | 7/1971 | De Boer et al. |
| 3,987,035 | A | 10/1976 | Rinehart, Jr. et al. |
| 4,075,339 | A | 2/1978 | Rinehart, Jr. et al. |
| 4,261,989 | A | 4/1981 | Sasaki et al. |
| 4,421,687 | A | 12/1983 | Hasegawa et al. |
| 4,421,688 | A | 12/1983 | Muroi et al. |
| 4,540,517 | A | 9/1985 | Tanida et al. |
| 5,387,584 | A | 2/1995 | Schnur |
| 5,932,566 | A | 8/1999 | Schnur et al. |
| 5,968,921 | A | 10/1999 | Gold |
| 6,245,759 | B1 | 6/2001 | Bilodeau et al. |
| 6,306,874 | B1 | 10/2001 | Fraley et al. |
| 6,313,138 | B1 | 11/2001 | Fraley et al. |
| 6,890,917 | B2 * | 5/2005 | Snader et al. ............... 514/183 |
| 6,946,456 | B2 | 9/2005 | Rosen et al. |
| 2002/0045570 | A1 | 4/2002 | Rosen et al. |
| 2004/0110662 | A1 | 6/2004 | Rosen et al. |
| 2004/0266746 | A1 | 12/2004 | Rosen et al. |
| 2005/0020534 | A1 | 1/2005 | Johnson, Jr. |
| 2005/0020556 | A1 | 1/2005 | Johnson, Jr. |
| 2005/0020557 | A1 | 1/2005 | Johnson, Jr. |
| 2005/0020558 | A1 | 1/2005 | Johnson, Jr. |
| 2005/0026893 | A1 | 2/2005 | Johnson, Jr. |
| 2005/0049263 | A1 | 3/2005 | Kasibhatla et al. |
| 2005/0054589 | A1 | 3/2005 | Johnson, Jr. |
| 2005/0054625 | A1 | 3/2005 | Johnson, Jr. |
| 2005/0203174 | A1 | 9/2005 | Santi et al. |
| 2005/0256183 | A1 | 11/2005 | Kasibhatla et al. |
| 2006/0079493 | A1 | 4/2006 | Fritz et al. |
| 2006/0252740 | A1 | 11/2006 | Johnson, Jr. |
| 2007/0142346 | A1 | 6/2007 | Johnson, Jr. |

FOREIGN PATENT DOCUMENTS

| EP | 0 919 244 | 6/1999 |
| JP | 55-111419 | 8/1980 |
| JP | 55-111470 | 8/1980 |
| JP | 56-100766 | 8/1981 |
| JP | 57-163369 | 10/1982 |
| JP | 63-218620 | 9/1988 |
| JP | 4-46120 | 2/1992 |
| WO | WO-93/14215 | 7/1993 |
| WO | WO-98/51702 | 11/1998 |
| WO | WO-00/03737 | 1/2000 |
| WO | WO-00/37050 | 6/2000 |
| WO | WO-01/26693 | 4/2001 |
| WO | WO 01/32155 | * 10/2001 |
| WO | WO-02/09696 | 2/2002 |
| WO | WO-02/36171 | 5/2002 |
| WO | WO-02/36574 | 5/2002 |
| WO | WO-02/079167 | 10/2002 |
| WO | WO-02/087497 | 11/2002 |
| WO | WO-03/026571 | 4/2003 |
| WO | WO-03/050295 | 6/2003 |
| WO | WO-03/066005 | 8/2003 |
| WO | WO-03/082266 | 10/2003 |
| WO | WO-03/089006 | 10/2003 |

OTHER PUBLICATIONS

Anderson, Targeting host-tumour interactions in myeloma therapies, Teaching Lectures (2003) S6, no. 11.
Blagoskylonny et al., Leukemia (2001) 15:1537-1543.
Chem. Abstracts 130:291581, van der Bosch et al. (1999), assession No. 1999:254052 CAPLUS.
Grant and Roberts, Drug Resistance Updates (2003) 6:15-26.
Hurst et al., Clinical Cancer Research (1999) (supplemenet) 5(293):3788s.

(Continued)

*Primary Examiner*—Brian Kwon
(74) *Attorney, Agent, or Firm*—Morrison & Foerster LLP

(57) ABSTRACT

The invention relates to benzoquinone ansamycin analogs useful for the treatment of cancer and other diseases or conditions characterized by undesired cellular proliferation or hyperproliferation. Therapies involving the administration of such benzoquinone ansamycin analogs, optionally in combination with an inhibitor of an HSP90 client protein, are useful to treat cancer and non-cancerous disease conditions.

6 Claims, 6 Drawing Sheets

OTHER PUBLICATIONS

Jia et al., Blood (2003) 102(5):1824-1832.
Liao et al., Acta Pharmaceutica Sinica (2001) 36(8):569-575.
Münster et al., Clinical Cancer Research (2001) 7:2228-2236.
Neckers and Neckers, Expert Opin. Emerging Drugs (2002) 7(2):277-288.
Nguyen et al., Ann. Thorac. Surg. (2001) 72:371-379.
Nguyen et al., J. Thorac. Cardiovasc. Surg. (1999) 118:908-915.
Rahmani et al., Cancer Research (2003) 63:8420-8427.
Rakitina et al., Cancer Research (2003) 63:8600-8605.
Russell et al., Clinical Cancer Research (2003) 9:3749-3755.
Sausville, Clinical Cancer Research (2001) 7:2155-2158.
Solit et al., Cancer Research (2003) 63:2139-2144.
Vasilevskaya et al., Cancer Research (2003) 63:3241-3246.
CITRI et al., EMBO Journal (2002) 21:2407-2417.
International Search Report for PCT/US02/24891, mailed on Nov. 28, 2003, 4 pages.
Kamal et al.; Nature (2003) 425:407-410.
Munster et al., Clinical Cancer Research (2001) 7:2228-2236.
Neckers and Lee, Nature (2003) 425:357-359.
Schnur et al., J. Med. Chem. (1995) 38:3806-3812.
Schnur et al., J. Med. Chem. (1995) 38:3813-3820.
Birgegard, European Journal of Cancer Supplements (2003) 1(5):S6.
U.S. Appl. No. 10/856,342, filed May 27, 2004.
U.S. Appl. No. 10/856,344, filed May 27, 2004.
U.S. Appl. No. 10/856,696, filed May 27, 2004.
U.S. Appl. No. 10/856,703, filed May 27, 2004.
U.S. Appl. No. 10/856,742, filed May 27, 2004.
U.S. Appl. No. 10/857,166, filed May 27, 2004.
U.S. Appl. No. 10/857,605, filed May 27, 2004.

* cited by examiner geldanamycin 17-allylamino-17-desmethoxy-
geldanamycin
(17-AAG)

17-(2-dimethylaminoethyl)amino-1
7-desmethoxygeldanamycin
(17-DMAG)

R¹ =

R² =     H

Tarceva

Iressa

BIBX 1382

Gleevec

SU101

Lefunamide

Flavopiridol

CEP-701

UCN-01

BENZOQUINONE ANSAMYCINS

CROSS-REFERENCE TO RELATED APPLICATIONS

This application is a Divisional of U.S. patent application Ser. No. 10/212,962, filed on Aug. 5, 1999, now U.S. Pat. No. 6,872,715 which claims priority to U.S. Provisional Application 60/310,779, filed Aug. 6, 2001, entitled "Geldanamycin Analogs," and to U.S. Provisional Applications 60/389,225, filed Jun. 14, 2002; 60/393,929, filed Jul. 3, 2002; and 60/395,275, filed Jul. 12, 2002; each entitled "Recombinant Geldanamycin Polyketide Synthase Genes." Each of the above documents is incorporated herein by reference in their entireties.

STATEMENT OF GOVERNMENT INTEREST

The present invention was made in part under NIH Grant No. R43 CA96262-01. The United States government may have certain rights in this invention.

BACKGROUND

The clinical utility of many potential anti-cancer compounds is limited by undesired toxicity against non-target cells. Undesired toxicity in a drug is typically due to a lack of specificity, either in target tissue or in mechanism of action. If the drug target is present in normal as well as diseased tissues, then normal tissue as well as diseased tissue may be affected by the drug. The drug may also have multiple mechanisms of toxicity, one specific for diseased cells and the other non-specific. In either instance, there is often a dose-dependent difference in the actions of drugs against normal and diseased tissues, with the effects on diseased tissues being observed at lower concentrations than the effects on normal tissues. A major task of anti-cancer therapy is thus to determine the dosage at which the drug is therapeutically effective with minimal effects on normal tissues.

Phase I clinical trials are typically used to determine the maximum tolerated dose (MTD) of a potential anti-cancer compound, i.e., the maximum dose that can be safely administered without incurring toxicity. The difference between the MTD and the therapeutically effective dose is known as the therapeutic window. For a large number of anti-cancer agents, the MTD is very close to the therapeutically effective dose, i.e., the therapeutic window is very small. The MTD may even be lower than the therapeutically effective dose, making the agent unusable in the clinic.

Clinical anti-cancer therapy often involves attempting to achieve a delicate balance between effectiveness and undesired toxicity. Agents which synergize the action of a drug against diseased tissues while not affecting the toxicity against normal tissues could allow the effective use of doses of drug well below the MTD, thus increasing the therapeutic window and enhancing the safety and effectiveness of the therapy.

Geldanamycin (FIG. 1) is a benzoquinone ansamycin polyketide isolated from *Streptomyces geldanus*. Although originally discovered by screening microbial extracts for anti-bacterial and antiviral activity, geldanamycin was later found to be cytotoxic to certain tumor cells in vitro and to reverse the morphology of cells transformed by the Rous sarcoma virus to a normal state.

Geldanamycin's nanomolar potency and apparent specificity for aberrant protein kinase dependent tumor cells, as well as the discovery that its primary target in mammalian cells is the ubiquitous Hsp90 protein chaperone, has stimulated interest in the development of this anti-cancer drug. However, the association of hepatotoxicity with the administration of geldanamycin led to its withdrawal from Phase I clinical trials. As with several other promising anticancer agents, geldanamycin also has poor water solubility that makes it difficult to deliver in therapeutically effective doses.

More recently, attention has focused on 17-amino derivatives of geldanamycin, in particular 17-(allylamino)-17-desmethoxygeldanamycin (17-AAG; FIG. 1), that show reduced hepatotoxicity while maintaining Hsp90 binding. Certain 17-amino derivatives of geldanamycin, 11-oxogeldanamycin, and 5,6-dihydrogeldanamycin, are disclosed in U.S. Pat. Nos. 4,261,989; 5,387,584; and 5,932,566, each of which is incorporated herein by reference. Like geldanamycin, 17-AAG has limited aqueous solubility. This property requires the use of a solubilizing carrier, most commonly Cremophore® (BASF Aktiengesellschaft), a polyethoxylated castor oil which can result in serious side reactions in some patients.

Treatment of cancer cells with geldanamycin or 17-AAG causes a retinoblastoma protein-dependent G1 block, mediated by down-regulation of the induction pathways for cyclin D-cyclin dependent cdk4 and cdk6 protein kinase activity. Cell cycle arrest is followed by differentiation and apoptosis. G1 progression is unaffected by geldanamycin or 17-AAG in cells with mutated retinoblastoma protein; these cells undergo cell cycle arrest after mitosis, again followed by apoptosis.

The mechanism of action of benzoquinone ansamycins appears to be via binding to Hsp90 and subsequent degradation of Hsp90-associated client proteins. Among the most sensitive client protein targets of the benzoquinone ansamycins are the Her kinases (also known as ErbB), Raf, Met tyrosine kinase, and the steroid receptors. Hsp90 is also involved in the cellular response to stress, including heat, radiation, and toxins. Certain benzoquinone ansamycins, such as 17-AAG, have thus been studied to determine their interaction with cytotoxins that do not target Hsp90 client proteins.

U.S. Pat. Nos. 6,245,759; 6,306,874; and 6,313,138, each of which is incorporated herein by reference, disclose compositions comprising certain tyrosine kinase inhibitors together with 17-AAG and methods for treating cancer with such compositions. Münster et al., "Modulation of Hsp90 function by ansamycins sensitizes breast cancer cells to chemotherapy-induced apoptosis in an RB- and schedule-dependent manner," *Clinical Cancer Research* (2001) 7: 2228-2236, discloses that 17-AAG sensitizes cells in culture to the cytotoxic effects of paclitaxel and doxorubicin. The Münster reference further discloses that the sensitization towards paclitaxel by 17-AAG is schedule-dependent in retinoblastoma protein-producing cells due to the action of these two drugs at different stages of the cell cycle: treatment of cells with a combination of paclitaxel and 17-AAG is reported to give synergistic apoptosis, while pretreatment of cells with 17-AAG followed by treatment with paclitaxel is reported to result in abrogation of apoptosis. Treatment of cells with paclitaxel followed by treatment with 17-AAG 4 hours later is reported to show a synergistic effect similar to coincident treatment.

Citri et al., "Drug-induced ubiquitylation and degradation of ErbB receptor tyrosine kinases: implications for cancer chemotherapy," *EMBO Journal* (2002) 21: 2407-2417, discloses an additive effect upon co-administration of geldanamycin and an irreversible protein kinase inhibitor, CI-1033, on growth of ErbB2-expressing cancer cells in vitro. In contrast, an antagonistic effect of CI-1033 and an anti-ErbB2 antibody, Herceptin, is disclosed.

Thus, while there has been a great deal of research interest in the benzoquinone ansamycins, particularly geldanamycin and 17-AAG, there remains a need for effective therapeutic regimens to treat cancer or other diseases or conditions characterized by undesired cellular hyperproliferation using such compounds, whether alone or in combination with other agents. If water-soluble benzoquinone ansamycins were available, such compounds might be more readily formulated and more effective in clinical treatment without dangerous hepatotoxicity. If effective therapeutic treatment regimens were available for administering the benzoquinone ansamycins with other proven anti-cancer compounds, there could be new and more effective means of treating cancer. If the potential of using a benzoquinone ansamycin to lower the effective dose of another anti-cancer agent could be realized, then not only could less expensive therapies be made available (since less drug would need to be administered) but also, and more importantly, one could use drugs that have previously not been useful in chemotherapy due to their narrow therapeutic window. Thus, there is an unmet need for synergists of anti-cancer compounds that allow for administration of doses significantly below the maximum tolerated dose while maintaining therapeutic effectiveness, along with appropriate dosing schedules for combination therapy. The present invention meets such needs in that it provides novel benzoquinone ansamycins and provides methods for using these novel compounds as well as known compounds in single-agent and combination therapies for the treatment of cancer and other diseases or conditions characterized by undesired cellular hyperproliferation.

SUMMARY OF THE INVENTION

The present invention provides compounds, methods for their preparation and intermediates thereto, and methods for the use of these compounds in the treatment of diseases or conditions characterized by undesired cellular proliferation or hyperproliferation.

In one aspect, the invention provides novel benzoquinone ansamycins related to geldanamycin. These analogs are prepared through chemical manipulation and/or genetic engineering. Compounds having improved solubility properties and compounds having conformations optimized to bind Hsp90 are also provided.

In a second aspect, the invention provides genetically engineered forms of the geldanamycin polyketide synthase biosynthetic gene cluster, vectors comprising said gene clusters, host cells comprising said vectors, and methods for the production of geldanamycin analogs using said host cells.

In a third aspect, the invention provides compositions comprising benzoquinone ansamycins for the treatment of diseases or conditions characterized by undesired cellular proliferation or hyperproliferation. In certain embodiments, the disease is cancer.

In a fourth aspect, the invention provides combination therapies comprising the use of a benzoquinone ansamycin and a second agent for use in the treatment of diseases or conditions characterized by undesired cellular hyperproliferation. In certain embodiments, the disease is cancer. In certain embodiments, the second agent is an inhibitor of an Hsp90 client protein. In certain embodiments, the second agent is a protein kinase inhibitor. In certain embodiments, the second agent is a microtubule stabilizing agent. In certain embodiments, the second agent is a cytotoxic drug. In one embodiment, the second agent has been approved by the Federal Drug Administration as a stand-alone agent for the treatment of cancer. In another embodiment, the second agent has not entered or has entered but not progressed through clinical trials in the United States due to overt toxicity or narrow therapeutic window.

In a fifth aspect, the invention provides methods for preventing undesired cell adhesion and growth on devices for in vivo use. These devices include stents, catheters, prostheses and the like.

DETAILED DESCRIPTION OF THE INVENTION

Figure 1:
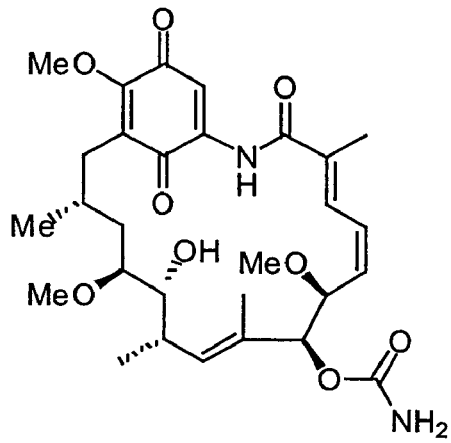
FIG. 1 shows the structures of various naturally-occurring benzoquinone ansamycins as well as 17-AAG anf 17-DMAG.
Figure 1:
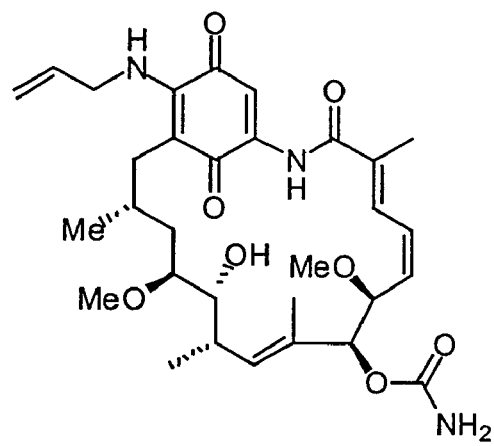
Figure 1:
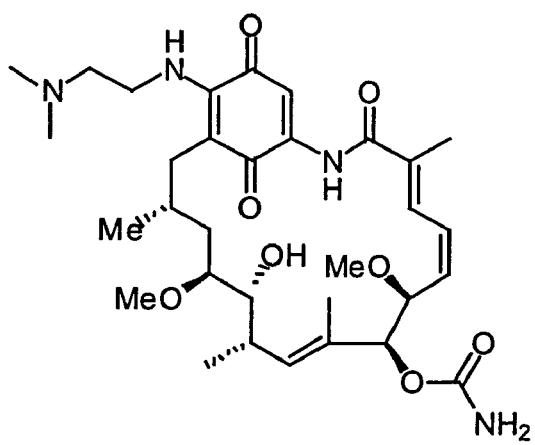

The present invention provides compounds, intermediates thereto, and methods for the use of these compounds in the treatment of diseases or conditions characterized by undesired cellular hyperproliferation.

Statements regarding the scope of the present invention and definitions of terms used herein are listed below. The definitions apply to the terms as they are used throughout this specification, unless otherwise limited in specific instances, either individually or as part of a larger group.

Where stereochemistry is not specifically indicated, all stereoisomers of the inventive compounds are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

Protected forms of the inventive compounds are included within the scope of this invention. A variety of protecting groups are disclosed, for example, in T. H. Greene and P. G. M. Wuts, Protective Groups in Organic Synthesis, Third Edition, John Wiley & Sons, New York (1999). The present invention includes within its scope prodrugs of the active compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in "Design of Prodrugs," H. Bundgaard ed., Elsevier, 1985.

As used herein, the terms "benzoquinone ansamycin" refers to a compound comprising a benzoquinone nucleus connected at two non-adjacent positions by a macrocyclic lactam. Specific examples of naturally-occurring benzoquinone ansamycins include but are not limited to geldanamycin, herbimycin, macbecin, mycotrienes, and ansamitocin. The term "geldanamycin analog" refers to a type of benzoquinone ansamycin that can be derived from geldanamycin by chemical manipulation or by manipulation of the geldanamycin biosynthetic gene cluster, such as 17-allylamino-17-desmethoxygeldanamycin (17-AAG), 17-(2-dimethylaminoethyl)amino-17-desmethoxygeldanamycin (17-DMAG), or a compound having a structure shown in formula (I).

As used herein, the term "aliphatic" refers to saturated and non-aromatic unsaturated straight chain, branched chain, cyclic, or polycyclic hydrocarbons. Illustrative examples of aliphatic groups include alkyl, alkenyl, alkynyl, cycloalkyl, cycloalkenyl, and cycloalkynyl groups. The term "alkyl" refers to a straight or branched chain saturated hydrocarbon substituent. "Alkenyl" refers to a straight or branched chain hydrocarbon substituent with at least one carbon-carbon double bond. "Alkynyl" refers to a straight or branched chain hydrocarbon substituent with at least one carbon-carbon triple bond.

The term "aryl" refers to monocyclic or polycyclic groups having at least one aromatic ring structure that include preferably one to fourteen carbon atoms. Illustrative examples of aryl groups include but are not limited to: naphthyl, phenyl, tetrahydronaphthyl, and the like.

The term "heteroaryl" refers to monocyclic or polycyclic groups having at least one aromatic ring structure and that include one or more heteroatoms and preferably one to fourteen carbon atoms. Illustrative examples of heteroaryl groups include but are not limited to: furanyl, imidazolyl, indanyl, indolyl, indazolyl, isoxazolyl, isoquinolyl, oxazolyl, oxadiazolyl, pyrazinyl, pyridyl, pyrimidinyl, pyrrolyl, pyrazolyl, quinolyl, quinoxalyl, tetrazolyl, thiazolyl, thienyl, and the like.

The aliphatic, aryl, and heteroaryl moieties may be substituted with one or more substituents, preferably from one to five substituents, more preferably from one to three substituents, and most preferably from one to two substituents, and as such are referred to as "substituted aliphatic," "substituted aryl," and "substituted heteroaryl." The definition of any substituent or variable at a particular location in a molecule is independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. Examples of suitable substituents include but are not limited to: aliphatic, haloaliphatic, halogen, aryl, heteroaryl, hydroxy, alkoxy, aryloxy, azido, thio, alkylthio, arylthio, amino, alkylamino, arylamino, acyl, carbamoyl, sulfonamido, nitro, cyano, carboxy, guanidine, and the like.

The term "haloaliphatic" refers to a substituted aliphatic group substituted by one or more halogens.

The terms "halo, "halogen," or "halide" refer to fluorine, chlorine, bromine, and iodine.

The term "acyl" refers to —C(=O)R, where R is an aliphatic group.

The term "alkoxy" refers to —OR, where R is an aliphatic group.

The term "aryloxy" refers to —OR, where R is an aryl group.

The term "carbamoyl" refers to —O(C=O)NRR', where R and R' are independently H, aliphatic, or aryl groups.

The term "alkylamino" refers to —NHR, where R is an alkyl group. The term "dialkylamino" refers to —NRR', where both R and R' are alkyl groups.

The term "hydroxyalkyl" refers to —R—OH, where R is an aliphatic group.

The term "aminoalkyl" refers to —R—NH$_2$, where R is an aliphatic group. The term "alkylaminoalkyl" refers to —R—NH—R', where both R and R' are aliphatic groups. The term "dialkylaminoalkyl" refers to —R—N(R')—R", where R, R', and R" are aliphatic groups. The term "arylaminoalkyl" refers to —R—NH—R', where R is an aliphatic and R' is an aryl group.

The term "oxo" refers to a carbonyl oxygen (=O).

The term "isolated" as used herein means that the isolated material is in a preparation in which said material forms a major component of the preparation, such as constituting about 50%, about 60%, about 70%, about 80%, about 90%, about 95%, about 99%, or more by weight of the components in the preparation.

The term "subject" as used herein, refers to an animal, typically a mammal or a human, that has been the object of treatment, observation, and/or experiment. When the term is used in conjunction with administration of a compound or drug, then the subject has been the object of treatment, observation, and/or administration of the compound or drug.

The term "therapeutically effective amount" as used herein, means that amount of active compound or pharmaceutical agent that elicits the biological or medicinal response in a cell culture, tissue system, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable salt" refers to a salt of one or more compounds. Suitable pharmaceutically acceptable salts of compounds include acid addition salts which may, for example, be formed by mixing a solution of the compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The term "pharmaceutically acceptable ester" refers to an ester that hydrolyzes under physiologically relevant conditions to produce a compound or a salt thereof. Illustrative examples of suitable ester groups include but are not limited to formates, acetates, propionates, butyrates, succinates, and ethylsuccinates.

The term "client protein" refers to a protein that interacts with a chaperone, for example Hsp90. In one aspect, this interaction with a chaperone is useful or required either for proper folding or for stabilization and maintenance. In another aspect, the chaperone forms the core of a functional receptor complex. In both of these aspects, the interaction with the chaperone may be direct or mediated through one or more other proteins. Table 1 below provides an illustrative list of the client proteins of Hsp90. The term "clientele" refers to the complete set of client proteins for a chaperone.

TABLE 1

Illustrative list of Hsp90 client proteins

| Client protein | Function |
| --- | --- |
| Steroid Hormone Receptors | |
| Glucocorticoid receptor | ligand-mediated gene transcription |
| Estrogen receptor | ligand-mediated gene transcription |
| Androgen receptor | ligand-mediated gene transcription |
| Progesterone receptor | ligand-mediated gene transcription |
| Protein Kinases | |
| c-SRC, v-SRC | signal transduction |
| LCK | T-cell development & function |
| WEE1 | Cell cycle regulation (G2) |
| MYT1 | Cell cycle regulation (G2) |
| ErbB2 (Her-2) | Signal transduction |
| EGFR (ErbB1) | Signal transduction |
| FPS/FES | Cell proliferation |
| c-RAF-1, v-RAF-1 | MAPK signaling |
| MEK | MAPK signaling |
| Casein kinase 2 | pleiotropic kinase |
| CDK4 | Cell cycle regulation (G1) |
| AKT (PKB) | PI3 kinase signaling |
| Death domain kinase RIP | TNF-mediated necrosis |
| Bcr-ABL | myeloid leukemia pathogenesis |
| PIM-1 | cytokine-mediated proliferation |
| MOK | MAPK signaling |
| Polo-1 kinase (PLK) | Cell cycle regulation (G2/M) |
| Focal adhesion kinase (FAK) | actin-based cell motility |
| c-MET | HGF/SF-MET motility signaling |
| eIF2 kinase | transcriptional regulation |
| Other Client Proteins | |
| Mutant p53 | cell cycle checkpoint protein mutant |
| Hepatitis B reverse transcriptase | viral transcription |
| hTERT (telomerase subunit) | cell mortality, senescence |
| βγ subunits of trimeric G proteins | signal transduction |
| endothelial NOS | NO synthesis |
| calcineurin | $Ca^{2+}$-dependent signaling |
| tubulin | microtubule formation |
| HIF-1α | hypoxia-induced angiogenesis |
| Retinoblastoma protein | cell cycle regulation (G1/S) |
| Tumor necrosis factor receptor 1 | TNF-mediated apoptosis |
| Cystic fibrosis transmembrane conductance regulator | Ion channel/cystic fibrosis |
| Immunoglobulin chains | Immune response |
| Fanconi anemia protein | hematopoiesis |
| Apoprotein B | atherosclerosis |
| Aryl hydrocarbon receptor | gene transcription |
| SV40 T antigen | viral oncogene |

In one aspect of the invention, geldanamycin analogs having the formula (I) are provided:

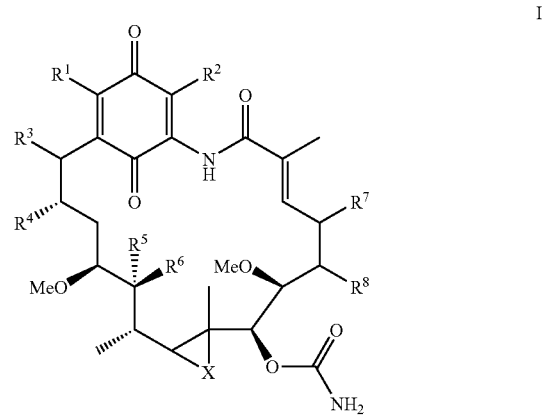

I wherein $R^1$ is MeO, $(CH_2)_3N$ or $R^9$—NH, wherein $R^9$ is selected from the group consisting of H, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted $C_3$-$C_6$ cycloalkyl, piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl)ethyl, 2-(N-methyl-pyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl, or $R^6$ is H and $R^1$ and $R^5$ taken together form a group of the formula NH-Z-O, wherein Z is a linker comprised of from 1 to 6 carbon atoms and 0 to 2 nitrogen atoms and wherein the O is attached at the position of $R^5$; $R^2$ is selected from the group consisting of H, halogen, $OR^{10}$, $NHR^{10}$, $SR^{10}$, aryl, and heteroaryl, wherein $R^{10}$ is selected from the group consisting of substituted or unsubstituted $C_1$-$C_6$ alkyl, substituted or unsubstituted $C_1$-$C_6$ alkenyl, substituted or unsubstituted $C_1$-$C_6$ alkynyl, and substituted or unsubstituted $C_3$-$C_6$ cycloalkyl; $R^3$ is H, OH, or OMe; $R^4$ is H or Me; $R^5$ is OH or O—C(=O)—$CH_2NH_2$ and $R^6$ is H, or $R^5$ and $R^6$ taken together form =O or =N—$OR^{11}$, wherein $R^{11}$ is selected from the group consisting of H, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted $C_3$-$C_6$ cycloalkyl, aryl, or heteroaryl; $R^7$ is H and $R^8$ is H or OH, or $R^7$ and $R^8$ taken together form a bond; and X is O or a bond, with the provisos that when $R^3$ is H, $R^4$ is Me, and $R^7$ is H and $R^8$ is H or $R^7$ and $R^8$ taken together form a bond that either $R^6$ is H and $R^1$ and $R^5$ taken together form a group of the formula NH-Z-O, wherein Z is a linker comprised of from 1 to 6 carbon atoms and 0 to 2 nitrogen atoms and wherein the O is attached at the position of $R^5$, or that $R^1$ is $(CH_2)_3N$ or $R^9$—NH, wherein $R^9$ is selected from the group consisting of piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl)ethyl, 2-(N-methyl-pyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl; and that when $R^3$ is H and $R^4$ is Me that $R^7$ is H and $R^8$ is OH.

In one embodiment, compounds having formula (I) are provided wherein $R^1$ is $(CH_2)_3N$ or $R^9$—NH, wherein $R^9$ is selected from the group consisting of piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl)ethyl, 2-(N-methyl-pyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl; $R^2$ is selected from the group consisting of H, halogen, $OR^{10}$, $NHR^{10}$, $SR^{10}$, aryl, and heteroaryl, wherein $R^{10}$ is selected from the group consisting of substituted or unsubstituted $C_1$-$C_6$ alkyl, substituted or unsubstituted $C_1$-$C_6$ alkenyl, substituted or unsubstituted $C_1$-$C_6$ alkynyl, and substituted or unsubstituted $C_3$-$C_6$ cycloalkyl; $R^3$ is H, OH, or OMe; $R^4$ is H or Me; $R^5$ is OH or O—C(=O)—$CH_2NH_2$ and $R^6$ is H, or $R^5$ and $R^6$ taken together form =O or =N—$OR^{11}$, wherein $R^{11}$ is selected from the group consisting of H, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted $C_3$-$C_6$ cycloalkyl, aryl, or heteroaryl; $R^7$ is H and $R^8$ is H or OH, or $R^7$ and $R^8$ taken together form a bond; and X is O or a bond.

In one embodiment, compounds having formula (I) are provided wherein $R^1$ is $(CH_2)_3N$ or $R^9$—NH, wherein $R^9$ is selected from the group consisting of piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl)ethyl, 2-(N-methyl-pyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl; $R^2$ is H; $R^3$ is H, OH, or OMe; $R^4$ is H or Me; $R^5$ is OH or O—C(=O)—$CH_2NH_2$ and $R^6$ is H, or $R^5$ and $R^6$ taken together form =O or =N—$OR^{11}$, wherein $R^{11}$ is selected from the group consisting of H, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted $C_3$-$C_6$ cycloalkyl, aryl, or heteroaryl; $R^7$ is H and $R^8$ is H or OH, or $R^7$ and $R^8$ taken together form a bond; and X is O or a bond.

In one embodiment, geldanamycin analogs having improved solubility are provided resulting from chemical manipulation of geldanamycin to provide compounds having formula (I) wherein: $R^1$ is $(CH_2)_3N$ or $R^9$—NH, wherein $R^9$ is selected from the group consisting of H, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted $C_3$-$C_6$ cycloalkyl, piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl)ethyl, 2-(N-methyl-pyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl; $R^2$ is selected from the group consisting of H, halogen, $OR^{10}$, $NHR^{10}$, $SR^{10}$, aryl, and heteroaryl, wherein $R^{10}$ is selected from the group consisting of substituted or unsubstituted $C_1$-$C_6$ alkyl, substituted or unsubstituted $C_1$-$C_6$ alkenyl, substituted or unsubstituted $C_1$-$C_6$ alkynyl, and substituted or unsubstituted $C_3$-$C_6$ cycloalkyl; $R^3$ is H; $R^4$ is methyl; $R^5$ is OH or O—C(=O)—$CH_2NH_2$ and $R^6$ is H, or $R^5$ and $R^6$ taken together form =O or =N—OH; $R^7$ and $R^8$ are H, or $R^7$ and $R^8$ taken together form a bond; and X is O or a bond.

In another embodiment of the invention, compounds having formula (I) are provided wherein: $R^1$ is $R^9$—NH, wherein $R^9$ is selected from the group consisting of ethyl, 2-(dimethylamino)ethyl, 2-fluoro ethyl, 2,2-difluoro ethyl, 2-(N-methylpyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, 3-(4-morpholino)-1-propyl, 3-(dimethylamino)-1-propyl, 3-(dimethylamino)-2-propyl, 2-(dimethylamino)-1-propyl, and cyclopropyl-methyl; $R^2$ is H; $R^3$ is H; $R^4$ is methyl; $R^5$ is OH or O—C(=O)—$CH_2NH_2$ and $R^6$ is H, or $R^5$ and $R^6$ taken together form =O or =N—OH; $R^7$ and $R^8$ are H, or $R^7$ and $R^8$ taken together form a bond; and X is O or a bond.

In another embodiment of the invention, compounds having the structures:

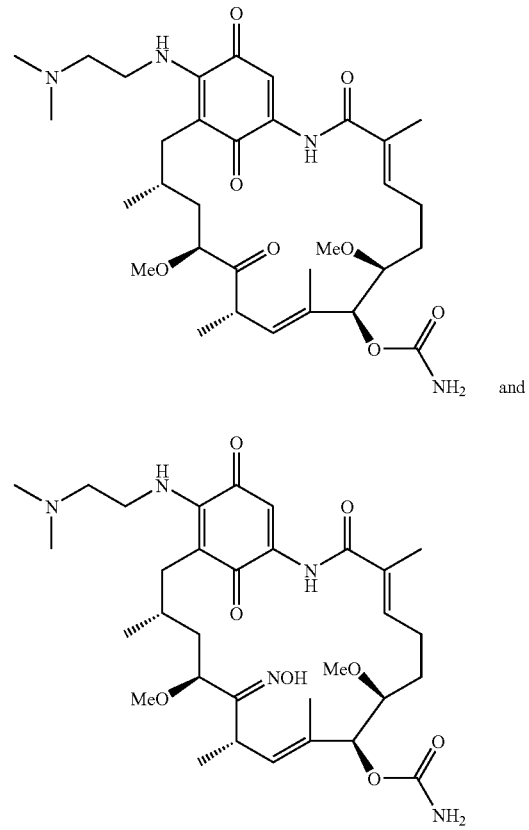

are provided.

In another embodiment, geldanamycin analogs having formula (I) are provided wherein $R^1$ is OMe; $R^2$ is H; $R^3$ is H, OH, or OMe; $R^4$ is H or methyl; $R^5$ is OH and $R^6$ is H; $R^7$ is H and $R^8$ is H or OH, or $R^7$ and $R^8$ taken together form a bond; and X is a bond, with the proviso that geldanamycin and 4,5-dihydrogeldanamycin are not included.

Other embodiments of the invention provide compounds having the formulas:

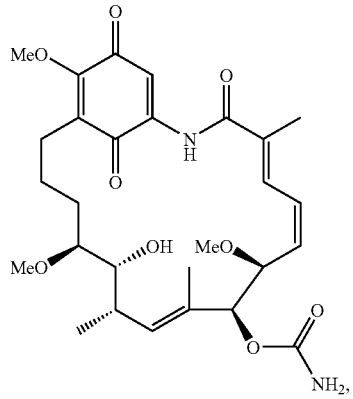

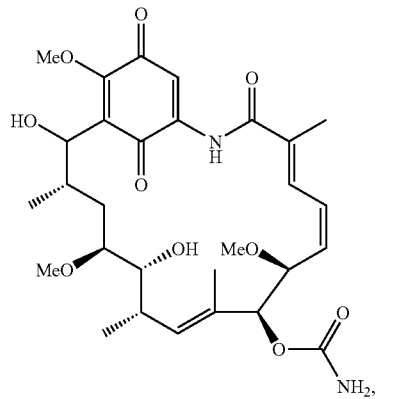

and

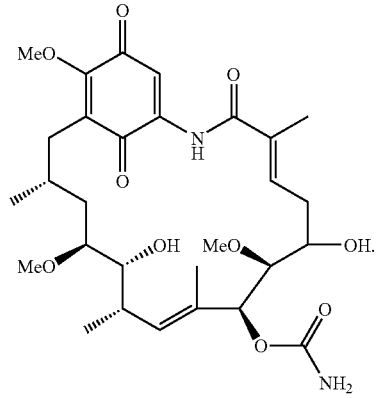

In other embodiments of the invention, the geldanamycin analogs described above serve as starting materials for chemical addition of solubilizing groups. In one embodiment, 15-hydroxygeldanamycin is derivatized to provide compounds having formula (I) wherein: $R^1$ is $(CH_2)_3N$ or $R^9$—NH, wherein $R^9$ is selected from the group consisting of H, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted $C_3$-$C_6$ cycloalkyl, piperidinyl, N-alkylpiperidinyl, hexahydropyranyl, furfuryl, tetrahydro-furfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl)ethyl, 2-(N-methyl-pyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl; $R^3$ is OH; $R^4$ is methyl; $R^5$ is OH or O—C(=O)—$CH_2NH_2$ and $R^6$ is H, or $R^5$ and $R^6$ taken together form =O or =N—OH; and $R^7$ and $R^8$ taken together form a bond; and X is O or a bond.

In another embodiment of the invention, 15-hydroxygeldanamycin is derivatized to provide compounds having formula (I) wherein: $R^1$ is $(CH_2)_3N$ or $R^9$—NH, wherein $R^9$ is selected from the group consisting of allyl, ethyl, 2-(dimethylamino)ethyl, 2-fluoroethyl, 2,2-difluoroethyl, 2-(N-methylpyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, 3-(4-morpholino)-1-propyl, 3-(dimethylamino)-1-propyl, 3-(dimethylamino)-2-propyl, 2-(dimethylamino)-1-propyl, and cyclopropylmethyl; $R^2$ is H; $R^3$ is OH; $R^4$ is methyl; $R^5$ is OH or O—C(=O)—$CH_2NH_2$ and $R^6$ is H, or $R^5$ and $R^6$ taken together form =O or =N—OH; $R^7$ and $R^8$ taken together form a bond; and X is O or a bond.

In another embodiment, 15-hydroxygeldanamycin analogs having the formulas

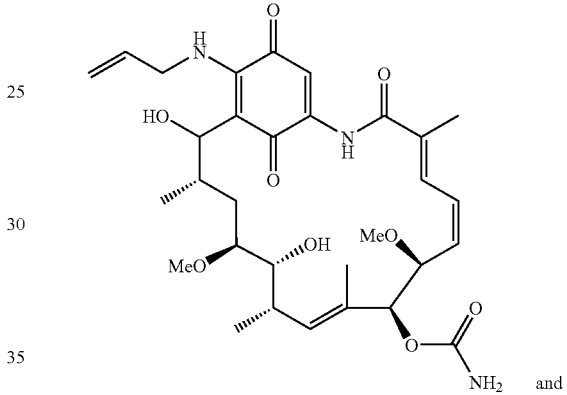

and

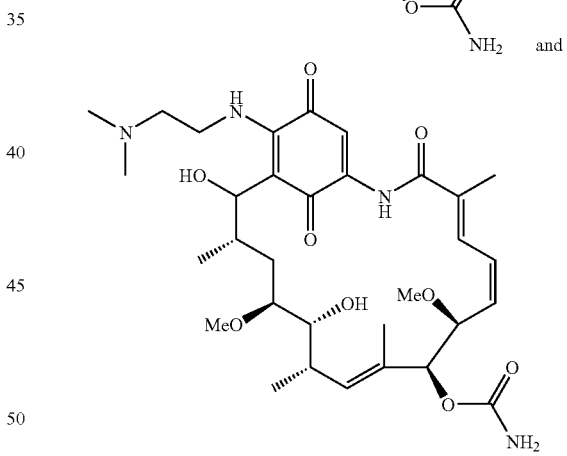

are provided.

In one embodiment, 28-desmethylgeldanamycin is derivatized to provide compounds having formula (I) wherein: $R^1$ is $(CH_2)_3N$ or $R^9$—NH, wherein $R^9$ is selected from the group consisting of H, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted $C_3$-$C_6$ cycloalkyl, piperidinyl, N-alkylpiperidinyl, hexahydropyranyl, furfuryl, tetrahydro-furfuryl, pyrrolidinyl, N-alkylpyrrolidinyl, piperazinylamino, N-alkylpiperazinyl, morpholinyl, N-alkylaziridinylmethyl, (1-azabicyclo[1.3.0] hex-1-yl)ethyl, 2-(N-methylpyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4- morpholino)-1-propyl; $R^2$ is selected from the group consisting of H, halogen, $OR^{10}$, $NHR^{10}$, $SR^{10}$, aryl, and heteroaryl, wherein $R^{10}$ is selected from the group consisting of substituted or unsubstituted $C_1$-$C_6$ alkyl, substituted or unsubstituted $C_1$-$C_6$ alkenyl, substituted or unsubstituted $C_1$-$C_6$ alkynyl, and substituted or unsubstituted $C_3$-$C_6$ cycloalkyl; $R^3$ is H; $R^4$ is H; $R^5$ is OH or O—C(=O)—$CH_2NH_2$ and $R^6$ is H, or $R^5$ and $R^6$ taken together form =O or =N—OH; and $R^7$ and $R^8$ taken together form a bond; and X is O or a bond.

In another embodiment of the invention, 28-desmethylgeldanamycin is derivatized to provide compounds having formula (I) wherein: $R^1$ is $(CH_2)_3N$ or $R^9$—NH, wherein $R^9$ is selected from the group consisting of allyl, ethyl, 2-(dimethylamino)ethyl, 2-fluoroethyl, 2,2-difluoroethyl, 2-(N-methylpyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, 3-(4-morpholino)-1-propyl, 3-(dimethylamino)-1-propyl, 3-(dimethylamino)-2-propyl, 2-(dimethylamino)-1-propyl, and cyclopropylmethyl; $R^2$ is H; $R^3$ is H; $R^4$ is H; $R^5$ is OH or O—C(=O)—$CH_2NH_2$ and $R^6$ is H, or $R^5$ and $R^6$ taken together form =O or =N—OH; R and $R^8$ taken together form a bond; and X is O or a bond.

In another embodiment, 28-desmethylgeldanamycin analogs having the formulas

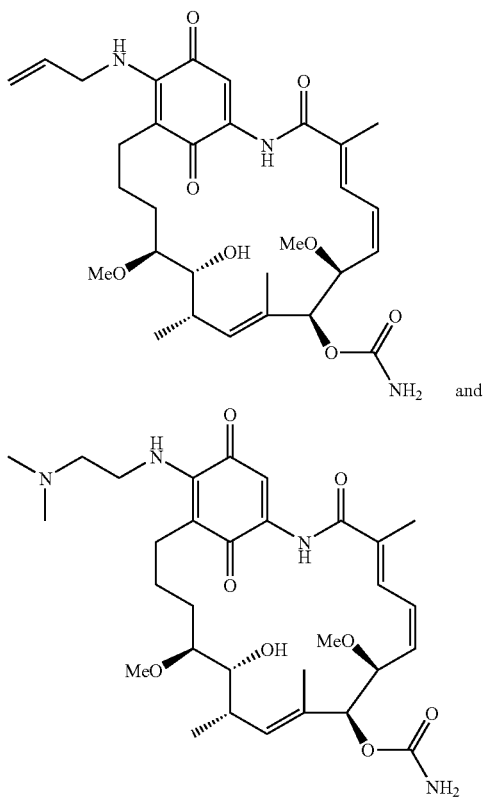

are provided.

In another embodiment, 4,5-dihydro-5-hydroxygeldanamycin is derivatized to provide compounds having formula (I) wherein: $R^1$ is $(CH_2)_3N$ or $R^9$—NH, wherein $R^9$ is selected from the group consisting of H, substituted or unsubstituted $C_1$-$C_6$ alkyl, substituted or unsubstituted $C_1$-$C_6$ alkenyl, substituted or unsubstituted $C_1$-$C_6$ alkynyl, substituted or unsubstituted $C_3$-$C_6$ cycloalkyl, piperidinyl, N-alkylpiperidinyl, hexahydropyranyl, furfuryl, tetrahydro-furfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl)ethyl, 2-(N-methylpyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl; $R^2$ is selected from the group consisting of H, halogen, $OR^{10}$, $NHR^{10}$, $SR^{10}$, aryl, and heteroaryl, wherein $R^{10}$ is selected from the group consisting of substituted or unsubstituted $C_1$-$C_6$ alkyl, substituted or unsubstituted $C_1$-$C_6$ alkenyl, substituted or unsubstituted $C_1$-$C_6$ alkynyl, and substituted or unsubstituted $C_3$-$C_6$ cycloalkyl; $R^3$ is H; $R^4$ is methyl; $R^5$ is OH or O—C(=O)—$CH_2NH_2$ and $R^6$ is H, or $R^5$ and $R^6$ taken together form =O or =N—OH; and $R^7$ is H; $R^8$ is OH; and X is O or a bond.

In another embodiment of the invention, 4,5-dihydro-5-hydroxygeldanamycin is derivatized to provide compounds having formula (I) wherein: $R^1$ is $(CH_2)_3N$ or $R^9$—NH, wherein $R^9$ is selected from the group consisting of allyl, ethyl, 2-(dimethylamino)ethyl, 2-fluoroethyl, 2,2-difluoroethyl, 2-(N-methylpyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, 3-(4-morpholino)-1-propyl, 3-(dimethylamino)-1-propyl, 3-(dimethylamino)-2-propyl, 2-(dimethylamino)-1-propyl, and cyclopropylmethyl; $R^2$ is H; $R^3$ is H; $R^4$ is methyl; $R^5$ is OH or O—C(=O)—$CH_2NH_2$ and $R^6$ is H, or $R^5$ and $R^6$ taken together form =O or =N—OH; $R^7$ is H; $R^8$ is OH; and X is O or a bond.

In another embodiment, 4,5-dihydro-5-hydroxygeldanamycin analogs having the formulas

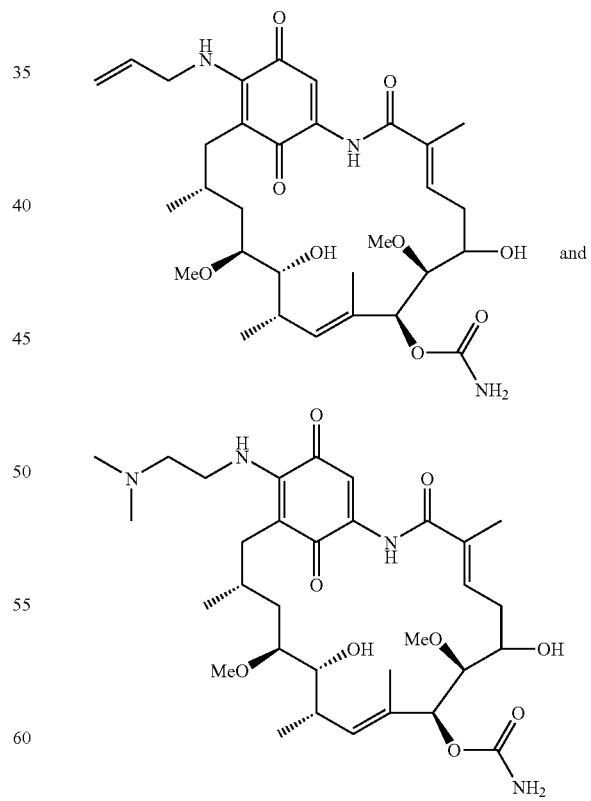

are provided.

In another aspect of the invention, conformationally constrained geldanamycin analogs are provided. In one embodiment, compounds having the formula (I) are provided wherein $R^1$ and $R^5$ taken together form a group of the formula NH-Z-O, wherein Z is a linker comprised of from 1 to 6 carbon atoms and 0 to 2 nitrogen atoms and wherein the O is attached at the position of $R^5$; $R^2$ is selected from the group consisting of H, halogen, $OR^{10}$, $NHR^{10}$, $SR^{10}$, aryl, and heteroaryl, wherein $R^{10}$ is selected from the group consisting of substituted or unsubstituted $C_1$-$C_6$ alkyl, substituted or unsubstituted $C_1$-$C_6$ alkenyl, substituted or unsubstituted $C_1$-$C_6$ alkynyl, and substituted or unsubstituted $C_3$-$C_6$ cycloalkyl; $R^3$ is H or OH; $R^4$ is H or methyl; $R^7$ is H and $R^8$ is H or OH, or $R^7$ and $R^8$ taken together form a bond; and X is O or a bond.

In one embodiment of the invention, compounds having formula (I) are provided wherein $R^1$ and $R^5$ taken together form a group of the formula NH—$(CH_2)_4$—O, NH—$CH_2CH$=$CHCH_2$—O, or NH—$CH_2CCCH_2$—O; $R^2$ is H; $R^3$ is H, OH, or OMe; $R^4$ is H or methyl; $R^7$ is H and $R^8$ is H or OH, or $R^7$ and $R^8$ taken together form a bond; and X is O or a bond.

In another embodiment of the invention, compounds having formula (I) are provided wherein $R^1$ and $R^5$ taken together form a group of the formula NH—$CH_2CH$=$CHCH_2$—O; $R^2$ is H; $R^3$ is H, OH, or OMe; $R^4$ is H or methyl; $R^7$ is H and $R^8$ is H or OH, or $R^7$ and $R^8$ taken together form a bond; and X is O or a bond.

In another embodiment of the invention, compounds having formula (I) are provided having the structures:

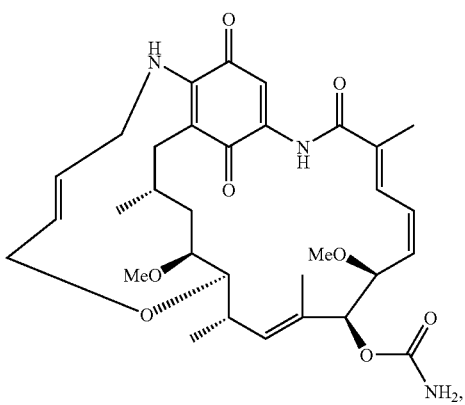

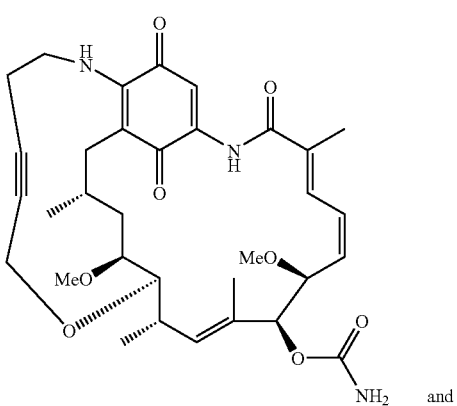
and

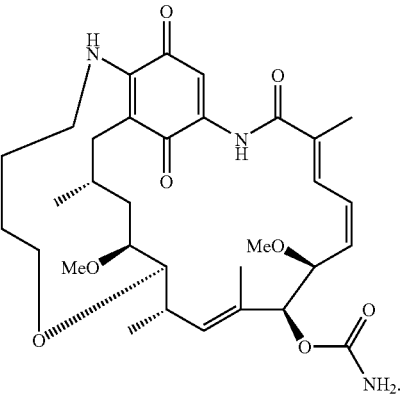

Figure 2:
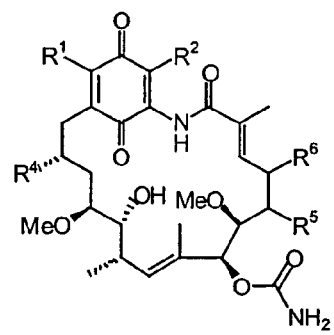
FIG. 2 shows particular embodiments of the compounds having formula (I) having groups with solubilizing functionalities.
Figure 2:
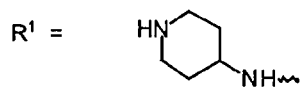
Figure 2:
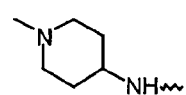
Figure 2:
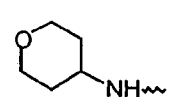
Figure 2:
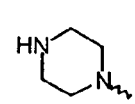
Figure 2:
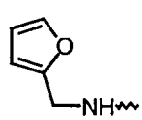
Figure 2:
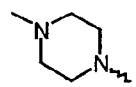
Figure 2:
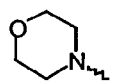
Figure 2:
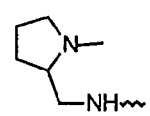
Figure 2:
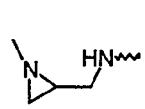
Figure 2:
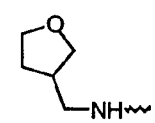
Figure 2:
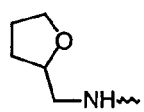
Figure 2:
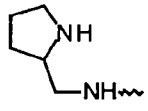
Figure 2:
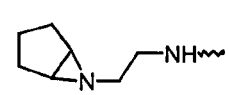
Figure 2:
Figure 2:
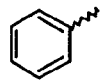
Figure 2:
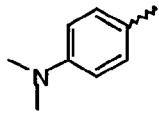
Figure 2:
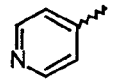
Figure 2:
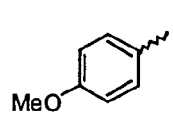
Figure 2:
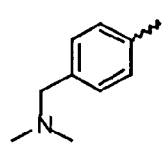
Figure 2:
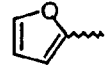

In another embodiment, the water-soluble analogs described above are subjected to conformational constraint to provide geldanamycin analogs having both improved solubility and improved specificity for Hsp90. Poor water solubility is a major factor limiting the clinical usefulness of geldanamycin and 17-AAG. Improvements in water solubility of a compound can be achieved according to the methods of the present invention either by addition of groups containing solubilizing functionalities to the compound or by removal of hydrophobic groups from the compound, so as to decrease the lipophilicity of the compound. Typical groups containing solubilizing functionalities are shown in FIG. 2 and include but are not limited to: 2-(dimethylaminoethyl) amino, piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl) ethyl, 2-(N-methylpyrrolidin-2-yl)ethyl, 2-(4-imidazolyl) ethyl, 2-(1-methyl-4-imidazolyl)ethyl, 2-(1-methyl-5-imidazolyl)ethyl, 2-(4-pyridyl)ethyl, and 3-(4-morpholino)-1-propyl.

Solubilizing groups are added to the geldanamycin analog by reaction of geldanamycin with amines, which results in the displacement of the 17-methoxy group by the amine as illustrated in Scheme 1 and exemplified in Example 1 (Schnur et al (1995) "Inhibition of the oncogene product p185$^{erbB-2}$ in Vitro and in Vivo by Geldanamycin and Dihydrogeldanamycin Derivatives,", *J. Med. Chem.* 38, 3806-3812; Schnur et al. (1995) "erbB-2 Oncogene Inhibition by Geldanamycin Derivatives: Synthesis, mechanism of Action, and Structure-Activity relationships," *J. Med. Chem.* 38, 3813-3820; Schnur et al., "Ansamycin derivatives as antioncogene and anticancer agents," U.S. Pat. No. 5,932,655; all of which are incorporated herein by reference). Typical amines containing solubilizing functionalities include 2-(dimethylamino)-ethylamine, 4-aminopiperidine, 4-amino-1-methylpiperidine, 4-aminohexahydropyran, furfurylamine, tetrahydrofurfurylamine, 3-(aminomethyl)-tetrahydrofuran, 2-(amino-methyl) pyrrolidine, 2-(aminomethyl)-1-methylpyrrolidine, 1-methylpiperazine, morpholine, 1-methyl-2(aminomethyl) aziridine, 1-(2-aminoethyl)-1-azabicyclo-[1.3.0]hexane, 1-(2-aminoethyl)piperazine, 4-(2-aminoethyl)morpholine, 1-(2-amino-ethyl)pyrrolidine, 2-(2-aminoethyl)pyridine, 2-fluoroethylamine, 2,2-difluoroethylamine, and the like.

SCHEME 1

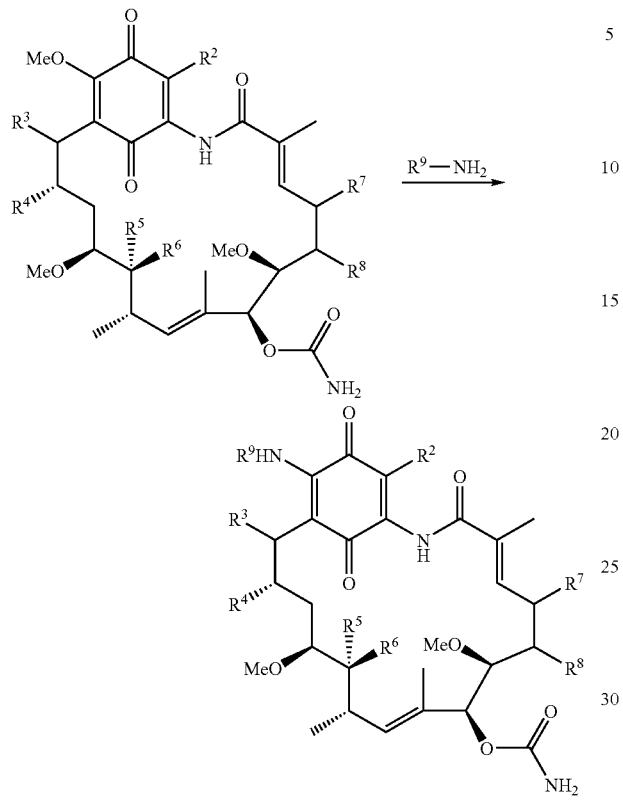

Similar solubilizing groups can be introduced by treatment of 19-bromo-geldanamycin or analogs with an amine containing a solubilizing substituent in accordance with the methods of the present invention, resulting in a 19-amino-substituted geldanamycin analog. The 19-bromo derivative is formed upon treatment of the geldanamycin analog with a suitable brominating reagent, such as pyridinium bromide perbromide (Schnur et al. 1995, *J. Med. Chem.* 38, 3806-3812; incorporated herein by reference). Reaction of 19-bromogeldanamycin with an arylboronic acid in the presence of a palladium catalyst according to the method of the present invention gives 19-aryl substituted geldanamycins as illustrated in Scheme 2. Boronic acids such as phenylboronic acid, (4-dimethyl-amino)phenyl-boronic acid, 4-pyridylboronic acid, 4-methoxyphenylboronic acid, 2-furylboronic acid, and 4-(dimethylaminomethyl)-phenylboronic acid and the like can also be used.

SCHEME 2

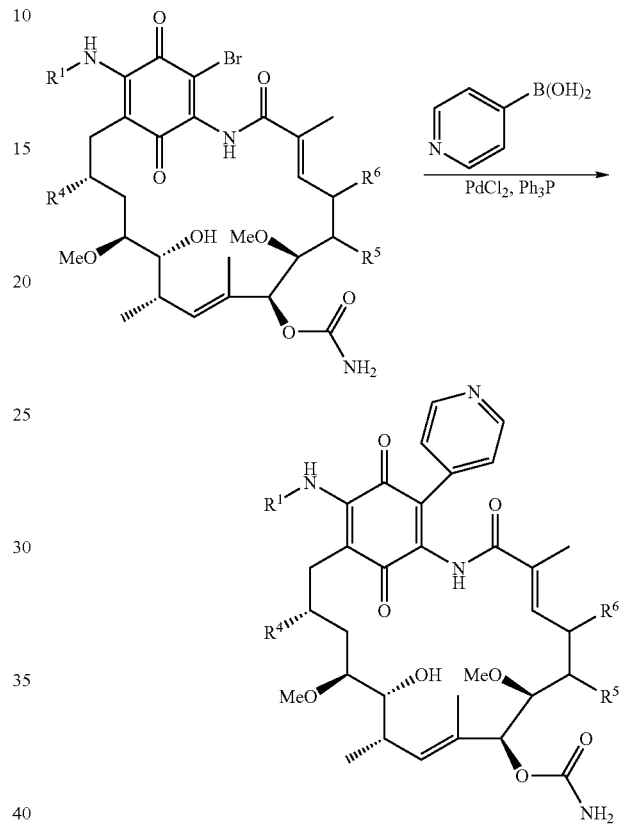

In another embodiment of the invention, the geldanamycin analogs are oxidized to produce the corresponding 11-oxogeldanamycin analogs as illustrated in Scheme 3.

SCHEME 3

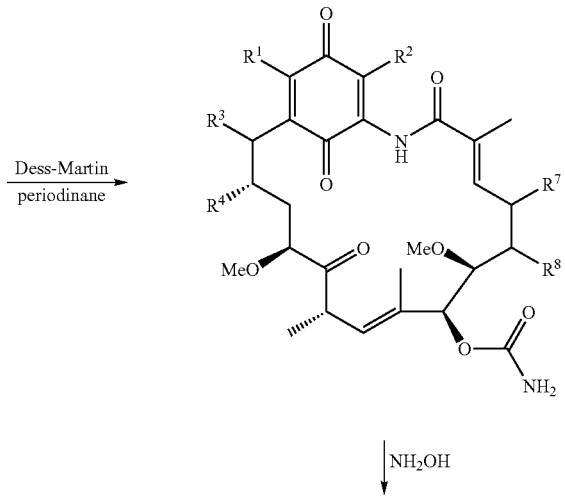

-continued

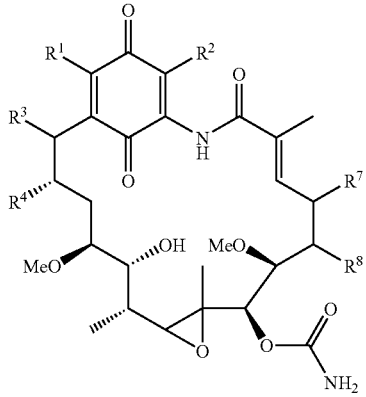 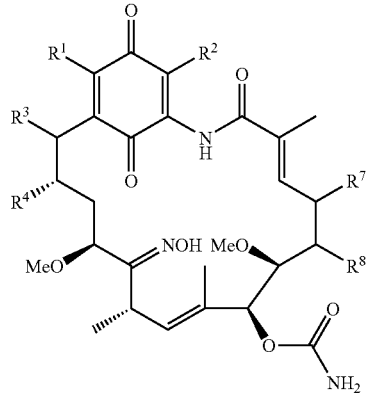

The 11-oxogeldanamycin analog resulting from oxidation of the 11-OH are converted into the 11-oximino analogs by reaction with hydroxylamine or an alkyoxylamine.

In another embodiment of the invention, the geldanamycin analog is treated with a peroxyacid, for example 3-chloroperoxybenzoic acid (mCPBA), to produce the 8,9-epoxide, as illustrated in Scheme 3.

In another aspect, the invention provides genetically engineered forms of the geldanamycin polyketide synthase biosynthetic gene cluster, vectors comprising said gene clusters, host cells comprising said vectors, and methods for the production of geldanamycin analogs using said host cells.

In one embodiment of the invention, substitution of the acyltransferase domain in module 1 of the geldanamycin PKS gene with one specific for malonyl-CoA instead of 2-methylmalonyl-CoA results in formation of 28-desmethyl-geldanamycin. The domain swap is created by introducing a malonyl-CoA specific acyltransferase domain from a heterologous PKS gene, for example from the rapamycin, tylosin, or FK520 PKS genes or the like, into the geldanamycin PKS locus by homologous recombination into a strain which produces geldanamycin, aided by a selectable antibiotic resistance gene, then isolating the recombinants resulting from double crossover events in which the wild-type acyltransferase domain is replaced with one specific for malonyl-CoA. Details of this are provided below in Example 5.

In another embodiment of the invention, the acyltransferase domain in module 1 of the geldanamycin PKS gene is mutagenized according to the methods described in Reeves et al., "Alteration of the substrate specificity of a modular polyketide synthase acyltransferase domain through site-directed mutagenesis," Biochemistry 2001, 40: 15464-15470, and in U.S. patent application Ser. No. 60/310,730, entitled "Alteration of the substrate specificity of a modular PKS AT domain," which is incorporated herein by reference. Details of this are provided below in Example 6.

In another embodiment of the invention, the coding sequence for the reduction cassette of module 6, which has both DH and KR domains, is replaced with a coding sequence for a reduction cassette that has only a KR domain. Details of this are provided below in Example 7.

In another embodiment of the invention, inactivation of the dehydraase domain in module 6 of the geldanamycin PKS gene by site-specific mutation of the wild-type domain in accord with the methods of the present invention results in production of 4,5-dihydro-5-hydroxygeldanamycin. Details of this are provided below in Example 8.

In another embodiment of the invention, a substantial portion of the nucleotide sequence in module 6 between the end of the AT domain is deleted to provide 4,5-dihydro-5-hydroxy-geldanamycin. Details of this are provided below in Example 9.

In another embodiment of the invention, the dehydratase domain of module 1 is replaced or inactivated as described above for module 6 to provide 15-hydroxy-geldanamycin. Details of this are provided below in Example 10.

In another embodiment of the invention, inactivation of the dehydratase domain in module 1 of the geldanamycin PKS gene by site-specific mutation of the wild-type domain in accord with the methods of the present invention results in production of 15-hydroxygeldanamycin. Details of this are provided below in Example 11.

It is also possible to express the geldanamycin gene cluster or mutated versions of the geldanamycin gene cluster prepared according to the methods of the invention in host cells other than the native geldanamycin producer. Methods for heterologous expression of PKS genes and host cells suitable for expression of these genes and production of polyketides are described, for example, in U.S. Pat. Nos. 5,843,718 and 5,830,750; PCT publications WO 01/31035 and WO 01/27306; and U.S. patent application Ser. Nos. 10/087,451; 60/355,211, entitled "Process and Metabolic Strategies for Improved Production of E. coli derived 6-deoxyerythronolide B," by inventors Pfeifer and Khosla; and 60/396,513, entitled "Metabolic Pathways for Starter Units in Polyketide Biosynthesis in E. Coli" by inventors Kealey, Dayem, and Santi; each of which is incorporated herein by reference.

Inactivation of dehydratase domains in accord with the methods of the present invention may also be obtained through random mutagenesis of the organism that normally produces geldanamycin. In this instance, spores of the producing organism can be either treated with a chemical mutagen, for example 1-methyl-3-nitro-1-nitrosoguanidine (MNNG), dimethylsulfate, or the like, or with mutagenic levels of radiation, for example ultraviolet radiation. The surviving spores are then allowed to grow on a suitable medium, and the resulting cultures are analyzed, for example by LC-mass spectrometry, for the presence of the desired new geldanamycin analog. Methods for the random mutagenesis of Streptomyces are described in Kieser et al, "Practical Streptomyces Genetics," The John Innes Foundation, Norwich (2000), which is incorporated herein by reference.

In accordance with the methods of the present invention, replacement of other acyltransferase domains in the geldanamycin PKS can be used to generate the respective desmethyl or desmethoxy analogs, and replacement of other dehydratase domains with inactive versions can be used to generate the corresponding dihydro-hydroxy analogs. Such analogs are expected to be more water-soluble, as they have fewer lipophilic substituents (28-desmethylgeldanamycin) or have additional hydrophilic substituents (4,5-dihydro-5-hydroxygeldanamycin or 15-hydroxygeldanamycin).

By using the geldanamycin analogs produced by genetic engineering of the geldanamycin PKS in accord with the methods of the present invention as described above, the afore-mentioned chemical transformations can be used to convert the analogs into more water-soluble, more potent, more specific inhibitors of Hsp90. Such compounds thus may overcome the necessity of using toxic vehicles such as Cremophore® in their administration, and show improved selectivity and reduced side-effects. In one embodiment of the invention, a geldanamycin analog prepared by genetic engineering is reacted with an amine as illustrated in Scheme 1 above.

Ring-forming olefin metathesis of 11-O-allyl-17-allylamino-17-desmethoxy-geldanamycin or similar analogs generates conformationally constrained benzoquinone ansamycins structure in accordance with the methods of the present invention. In one embodiment of the invention, treatment of 17-AAG with an allylating reagent, such as allyl tert-butyl carbonate and a palladium catalyst, generates 11-O-allyl-17-allylamino-17-desmethoxy-geldanamycin, as illustrated in Scheme 4 and exemplified in Example 2.

Reaction of related geldanamycin analogs resulting from displacement of the 17-methoxy group with amines other than allylamine, e.g., but-3-en-1-ylamine and pent-4-en-1-ylamine, results in formation of the corresponding 17-butenylamino-11-O-allyl and 17-pentenylamino-11-O-allyl analogs in accordance with the methods of the present invention. Treatment of these 11-O-allyl compounds with an olefin metathesis catalyst, such as benzylidene bis(tricyclohexylphosphine)ruthenium dichloride, as illustrated in Scheme 5, results in linkage of the 11- and 17-positions through a carbon chain and constraint of the geldanamycin conformation. This is exemplified below in Example 3.

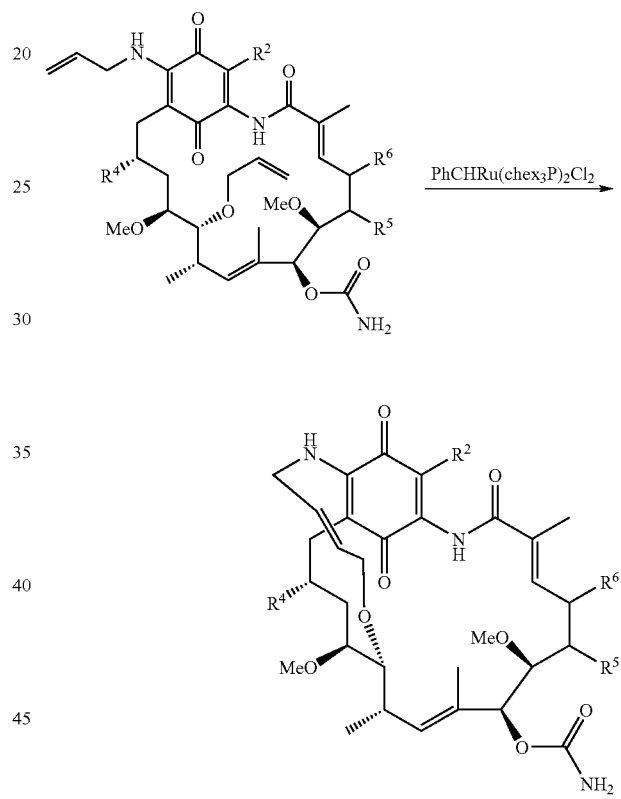

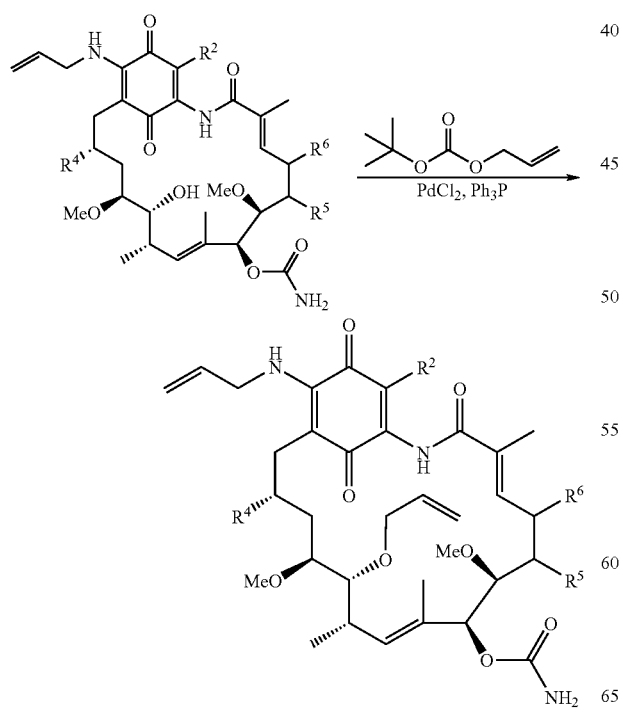

Alteration of the 11-O- and 17-N-groups in accord with the methods of the present invention allows for variation of the linker chain length. Thus, use of 11-O-allyl-17-allylamino-17-desmethoxygeldanamycin results in a 4-carbon linker, use of 11-O-allyl-17-(but-3-en-1-ylamino)-17-desmethoxygeldanamycin results in a 5-carbon linker, and use of 11-O-allyl-17-(pent-4-en-1-ylamino)-17-desmethoxygeldanamycin results in a 6-carbon linker. The carbon-carbon double bond of the linker can optionally be reduced by reduction, e.g. using diimide, to provide a saturated linker.

An alkynyl linker can be prepared according to the methods of the invention by treating geldanamycin or a geldanamycin analog with a bifunctional alkyne comprising an amino function at one end of the linker and a displaceable function, for example a halogen or sulfonate ester, at the other end. Reaction of geldanamycin or an analog with this bifunctional linker results first in displacement of the 17-methoxy group by the amine. Subsequent base treatment results in alkylation of the 11-hydroxyl as illustrated in Scheme 6.

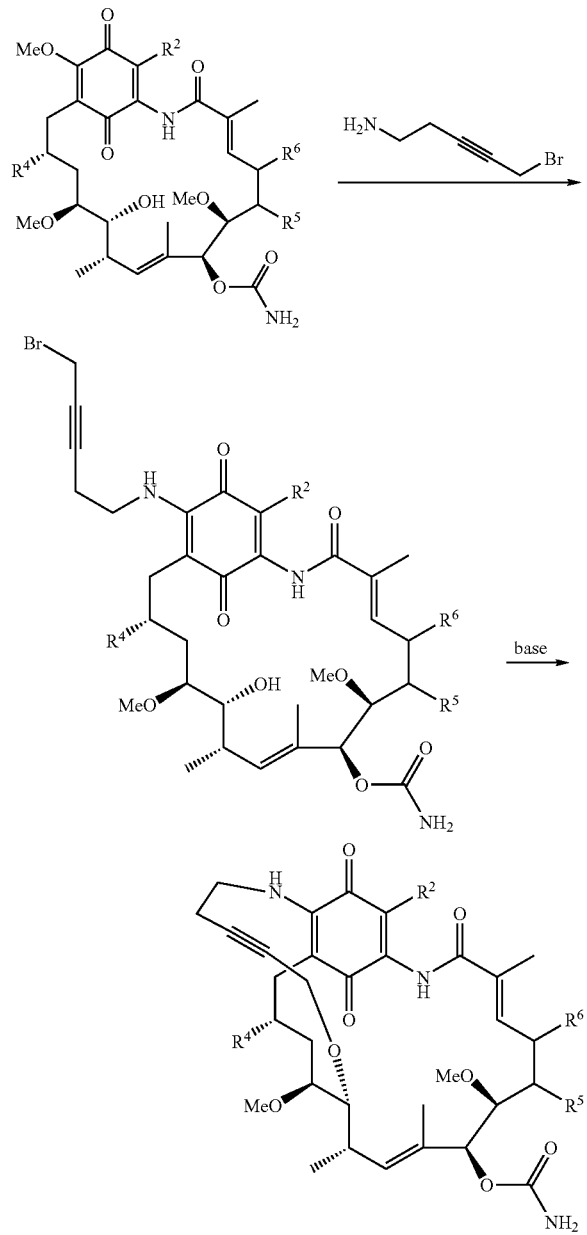

SCHEME 6

As described above, alteration of the linker lengths can be achieved through variation in the number of carbon atoms in the chain.

In another aspect of the invention, a composition comprising a benzoquinone ansamycin is used to treat a disease or condition characterized by undesired cellular proliferation or hyperproliferation. In one embodiment, the disease is cancer. In another embodiment, the disease is stenosis or restenosis. In another embodiment, the disease is psoriasis. In another embodiment, the disease is a neurodegenerative disease. In preferred embodiments, the benzoquinone ansamycin is a compound having formula (I), 17-AAG, or 17-DMAG.

In another aspect of the invention, a benzoquinone ansamycin is used in combination therapy with a second agent. In one embodiment, the second agent is an inhibitor of an Hsp90 client protein. Suitable Hsp90 client proteins include but are not limited to those listed in Table 1.

In one embodiment of the invention, a benzoquinone ansamycin is used in combination therapy with a protein kinase inhibitor. Suitable protein kinase inhibitors include but are not limited to the compounds listed in Table 2.

TABLE 2

Illustrative list of protein kinase inhibitors

| Compound | target | most advanced indication |
|---|---|---|
| Quinazolines and related heterocycles: | | |
| Iressa (ZD 1839) | EGFR | non-small cell lung cancer |
| Tarceva (OSI-774) | EGFR | ovarian cancer |
| GW2016 | EGFR | cancer |
| CI 1033 | EGFR | cancer |
| AZD6474 | VEGFR | solid tumors |
| Phenylamino-pyrimidines: | | |
| Gleevec (STI-571) | bcr-abl, others | chronic myelogenous leukemia |
| Pyrazolopyrimidines and pyrrolopyrimidines: | | |
| BIBX 1382 | EGFR | cancer |
| PKI 166 | EGFR | cancer |
| Indoles and oxindoles: | | |
| Semaxanib (SU5416) | flk-1/KDR kinase | advanced colorectal cancer |
| SU5402 | FGFR | cancer |
| Benzylidene malononitriles (tyrphostins): | | |
| Tyrphostin 25 | EGFR | cancer |
| SU101 | PDGFR | solid tumors |
| Leflunamide (SU0020) | PDGFR | solid tumors |
| Flavones: | | |
| Flavopiridol | cdk | cancer |
| B43-genistein | LYN | leukemia |
| Staurosporines: | | |
| CEP-701 | flt-3 | prostate, pancreatic cancers |
| CEP-2563 | trk | prostate, other cancers |
| UCN-01 (NSC638850) | | cancer |
| LY-333531 | PKCβ | diabetic complications |
| Antibodies, ribozymes: | | |
| Herceptin | Her-2 | breast cancer |
| Avastin antibody | VEGFR | advanced solid tumors |
| 2c4 antibody | Her-2 | solid tumors |
| IMC-1C11 | VEGFR | metastatic colorectal cancer |
| Cetuximab (C255) | EGFR | head & neck squamous cell cancer |
| ABX-EGF | EGFR | cancer |
| TheraCIM (H-R3) | EGFR | metastatic squamous cell carcinoma |
| SMART anti-VEGF | VEGFR | relapsed, refractory solid tumors |
| Angiozyme | VEGFR | cancer |

Figure 4:
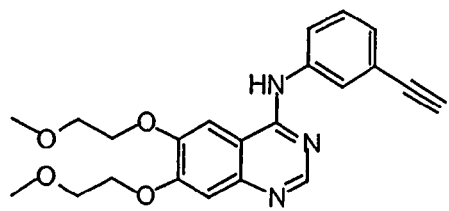
FIG. 4 shows the structures of representative protein kinase inhibitors.
Figure 4:
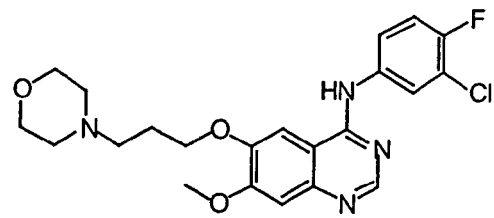
Figure 4:
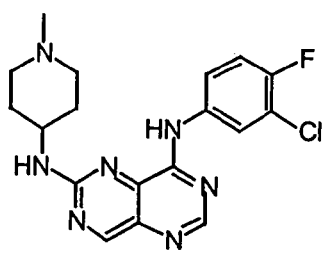
Figure 4:
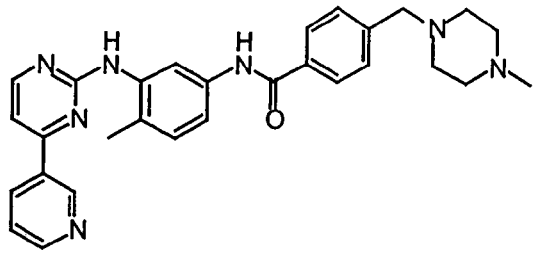
Figure 4:
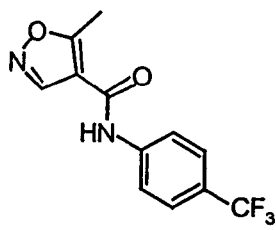
Figure 4:
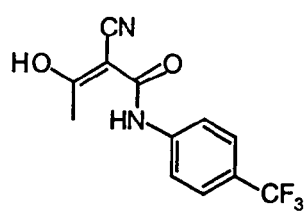
Figure 4:
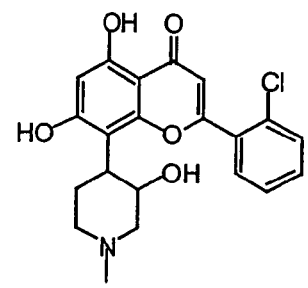
Figure 4:
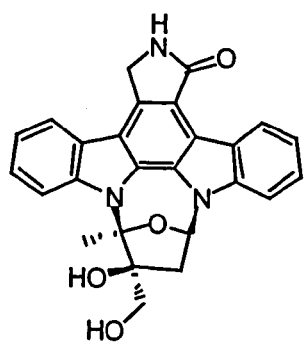
Figure 4:
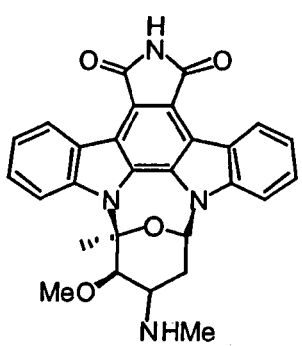

The protein kinase inhibitors listed in Table 2 may be classified according to their chemotypes, including: quinazolines, particularly 4-anilinoquinazolines such as Iressa (AstraZeneca; N-(3-chloro-4-fluorophenyl)-7-methoxy-6-[3-(4-morpholinyl)propoxy]-4-quinazolinamine) and Tarceva (Roche/Genentech; N-(3-ethynylphenyl)-6,7-bis(2-methoxyethoxy)-4-Quinazolinamine monohydrochloride); phenylamino-pyrimidines such as Gleevec (Novartis; 4-[(4-methyl-1-piperazinyl)methyl]-N-[4-methyl-3-[[4-(3-pyridinyl)-2-pyrimidinyl]amino]phenyl]benzamide); pyrrolo- and pyrazolopyrimidines such as BIBX 1382 (Boehringer Ingelheim; N8-(3-chloro-4-fluorophenyl)-N-2-(1-methyl-4-piperidinyl)-pyrimido[5,4-d]pyrimidine-2,8-diamine); indoles and oxindoles such as Semaxinib (Pharmacia; 3-[(3,5-dimethyl-1H-pyrrol-2-yl)methylene]-1, 3-dihydro-2H-Indol-2-one); benzylidene malononitriles; flavones such as flavopiridol (Aventis; 2-(2-chlorophenyl)-5,7-dihydroxy-8-[(3S,4R)-3-hydroxy-1-methyl-4-piperidinyl]-4H-1-benzopyran-4-one); staurosporines such as CEP-701 (Cephalon); antibodies such as Herceptin (Genentech); and ribozymes such as Angiozyme (Ribozyme Pharmaceuticals). Structures of representative protein kinase inhibitors are given in FIG. 4.

In another embodiment of the invention, a benzoquinone ansamycin is used in combination therapy with a microtubule stabilizing agent, including paclitaxel, epothilone, discodermolide, and laulimalide. In preferred embodiments, the benzoquinone ansamycin is a compound having the formula (I), 17-AAG, or 17-DMAG.

In another aspect, the present invention provides combination therapy methods for the treatment of diseases or conditions characterized by undesired cellular proliferation or hyperproliferation. Combination of two or more drugs in therapy may result in one of three outcomes: (1) additive, i.e., the effect of the combination is be equal to the sum of the effects of each drug when administered alone; (2) synergistic, i.e., the effect of the combination is greater than the sum of the effects of each drug when administered alone; or (3) antagonistic, i.e., the effect of the combination is less than the sum of the effects of each drug when administered alone. In one embodiment of the present invention, a subject is first treated with a substantially sub-toxic dose of a protein kinase inhibitor. After waiting for a period of time sufficient to allow development of a substantially efficacious response to the administration of the protein kinase inhibitor, a synergistic dose of a benzoquinone ansamycin is administered. Using this dosing schedule, a synergistic rather than additive effect of the two compounds is achieved. In one embodiment of the invention, the protein kinase inhibitor is a compound listed in Table 2, and the benzoquinone ansamycin is a compound having formula (I), 17-AAG, or 17-DMAG. In another embodiment of the invention, the protein kinase inhibitor is a drug approved by the Federal Drug Administration as a stand-alone treatment for cancer, and the benzoquinone ansamycin is a compound having formula (I), 17-AAG, or 17-DMAG. In one preferred embodiment, the cytotoxic agent is Iressa and the benzoquinone ansamycin is 17-AAG or 17-DMAG.

In another embodiment of the invention, a subject is first treated with a first sub-toxic dose of a protein kinase inhibitor. After waiting for a period of time sufficient to allow development of a substantially efficacious response of the protein kinase inhibitor, a formulation comprising a synergistic dose of a benzoquinone ansamycin together with a second sub-toxic dose of the protein kinase inhibitor is administered. In general, the appropriate period of time sufficient to allow development of a substantially efficacious response to the protein kinase inhibitor will depend upon the pharmacokinetics of the protein kinase inhibitor, and will have been determined during clinical trials of therapy using the protein kinase inhibitor alone. In one embodiment of the invention, the period of time sufficient to allow development of a substantially efficacious response to the protein kinase inhibitor is between 1 hour and 96 hours. In another embodiment of the invention, the period of time sufficient to allow development of a substantially efficacious response to the protein kinase inhibitor is between 2 hours and 48 hours. In another embodiment of the invention, the period of time sufficient to allow development of a substantially efficacious response to the protein kinase inhibitor is between 4 hours and 24 hours.

Figure 3A:
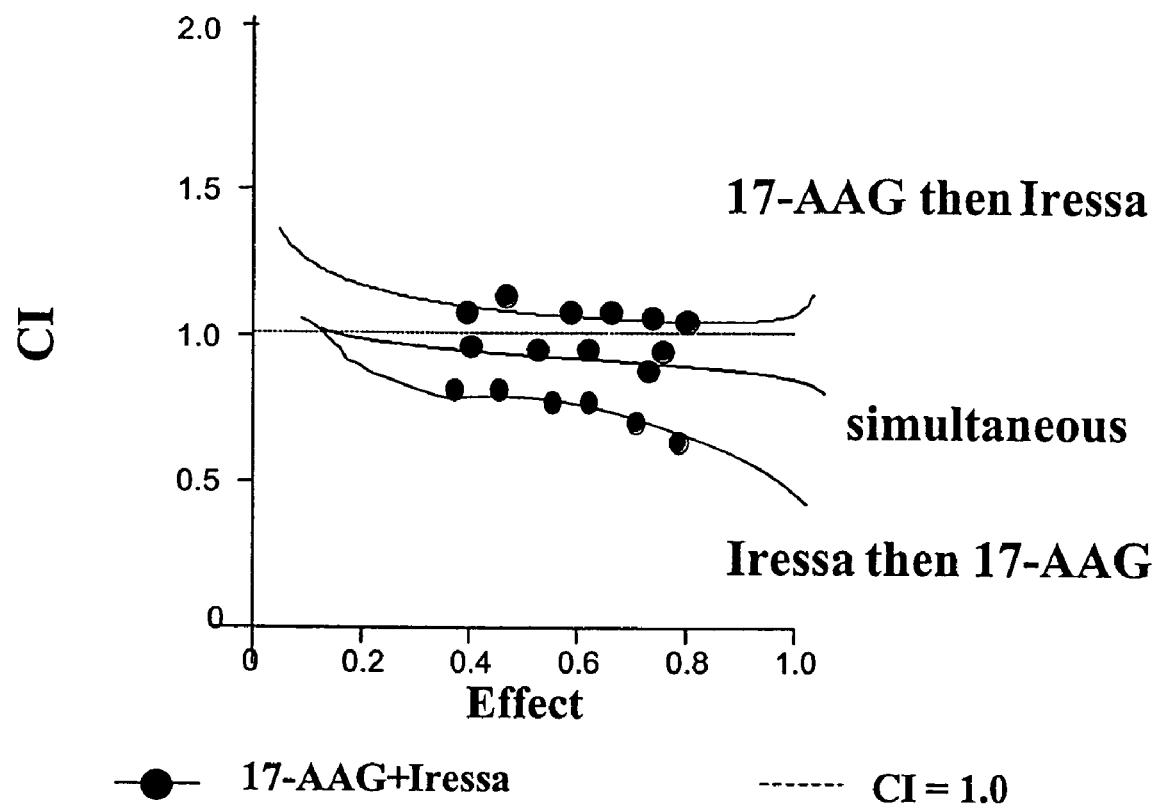
FIG. 3A-B show the results of treating SKBr3 cells with a benzoquinone ansamycin and the protein kinase inhibitor Iressa according to the methods of the present invention. Panel A shows results with 17-AAG. Panel B shows results with 17-DMAG.
Figure 3B:
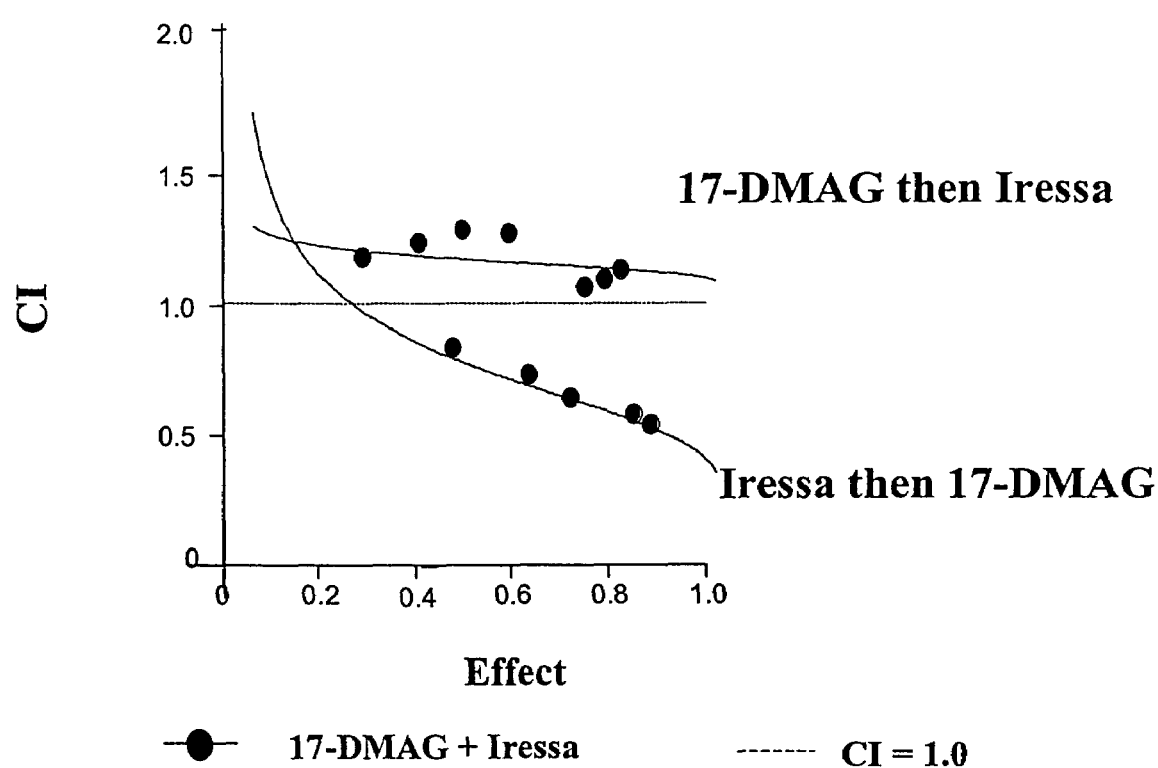

The protein kinase inhibitors are selected from but are not limited to those listed in Table 2. As demonstrated below in Example 4 and in FIG. 3A, pretreatment of cultured SKBr3 cells with the EGFR inhibitor Iressa followed by treatment with 17-AAG results in synergistic enhancement of the effects of Iressa. In contrast, the reverse order of administration or simultaneous administration results in an additive. Similar results were obtained with Iressa and 17-DMAG, as shown in FIG. 3B. Thus to obtain the optimal synergistic effect, it is necessary to provide the protein kinase inhibitor first, wait a period of time sufficient to allow development of a substantially efficacious response to the protein kinase inhibitor, and then provide the benzoquinone ansamycin.

In another embodiment, the subject is first treated with a sub-toxic dose of a benzoquinone ansamycin. After waiting for a period of time sufficient to allow development of a substantially efficacious response to the benzoquinone ansamycin, a synergistic dose of a microtubule stabilizing agent is administered. Using this dosing schedule, a synergistic rather than additive effect of the two compounds is achieved. Unexpectedly in light of Minster et al. "Modulation of Hsp90 function by ansamycins sensitizes breast cancer cells to chemotherapy-induced apoptosis in an RB- and schedule-dependent manner," *Clinical Cancer Research* (2001) 7: 2228-2236, pretreatment of cultured SKBr3 cells with the microtubule stabilizing agent paclitaxel followed by treatment with 17-AAG results in an additive effect, as demonstrated below in Example 4 and in FIG. 5. In contrast, the reverse order of administration results in a synergistic effect. Illustrative examples of microtubule stabilizing agents include but are not limited to paclitaxel, docetaxel, epothilone, discodermolide, and laulimalide.

The benzoquinone ansamycin may be a compound having formula (I), 17-AAG, or 17-DMAG. In one embodiment of the invention, the microtubule stabilizing agent is paclitaxel an epothilone, discodermolide or an analog, or laulimalide or an analog. In a preferred embodiment of the invention, the microtubule stabilizing agent is epothilone D.

In another embodiment of the invention, the combination therapy the second agent is a drug approved by the Federal Drug Administration as a stand-alone treatement for cancer, and the benzoquinone ansamycin is a compound having formula (I) or is 17-AAG or 17-DMAG. Illustrative examples of suitable drugs include but are not limited to 5-fluorouracil, methotrexate, vinblastine, cyclophosphamide, mechlorethamine, chlorambucil, Melphalan, Ifosfamide, bleomycin, mitomycin and doxorubicin.

In another embodiment, the combination therapy may include an agent or procedure to mitigate potential side effects from the combination therapy agents. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol. For those compositions that includes polyethoxylated castor oil such as Cremophor®, pretreatment with corticosteroids such as dexamethasone and methylprednisolone and/or $H_1$ antagonists such as diphenylhydramine HCl and/or $H_2$ antagonists may be used to mitigate anaphylaxis.

The dose of the second agent when used in combination therapy with a benzoquinone ansamycin is determined based on the maximum tolerated dose observed when the second agent is used as the sole therapeutic agent (the "MTD"). In one embodiment of the invention, the dose of the second agent when used in combination therapy with a benzoquinone ansamycin is the MTD. In another embodiment of the invention, the dose of the second agent when used in combination therapy with a benzoquinone ansamycin is between 1% of the MTD and the MTD. In another embodiment of the invention, the dose of the second agent when used in combination therapy with a benzoquinone ansamycin is between 5% of the MTD and the MTD. In another embodiment of the invention, the dose of the second agent when used in combination therapy with a benzoquinone ansamycin is between 5% of the MTD and 75% of the MTD. In another embodiment of the invention, the dose of the second agent when used in combination therapy with a benzoquinone ansamycin is between 25% of the MTD and 75% of the MTD.

Use of the benzoquinone ansamycin allows for use of a lower therapeutic dose of the second agent, thus significantly widening the therapeutic window for treatment. In one embodiment, the therapeutic dose of the second agent is lowered by at least 10%. In another embodiment, the therapeutic dose of the second agent is lowered from 10 to 20%. In another embodiment, the therapeutic dose of the second agent is lowered from 20 to 50%. In another embodiment, the therapeutic dose of the second agent is lowered from 50 to 200%. In another embodiment, the therapeutic dose of the second agent is lowered from 100 to 1000%.

The MTD for a compound is determined using methods and materials known in the medical and pharmacological arts, for example through dose-escalation experiments. One or more patients is first treated with a low dose of the compound, typically 10% of the dose anticipated to be therapeutic based on results of in vitro cell culture experiments. The patients are observed for a period of time to determine the occurrence of toxicity. Toxicity is typically evidenced as the observation of one or more of the following symptoms: vomiting, diarrhea, peripheral neuropathy, ataxia, neutropenia, or elevation of liver enzymes. If no toxicity is observed, the dose is increased 2-fold, and the patients are again observed for evidence of toxicity. This cycle is repeated until a dose producing evidence of toxicity is reached. The dose immediately preceding the onset of unacceptable toxicity is taken as the MTD.

The synergistic dose of the benzoquinone ansamycin used in combination therapy is determined based on the maximum tolerated dose observed when the benzoquinone ansamycin in used as the sole therapeutic agent. Clinical trials have determined an MTD for 17-AAG of 40 mg/m$^2$. In one embodiment of the invention, the dose of the benzoquinone ansamycin when used in combination therapy is the MTD. In another embodiment of the invention, the dose of the benzoquinone ansamycin when used in combination therapy is between 1% of the MTD and the MTD. In another embodiment of the invention, the dose of the benzoquinone ansamycin when used in combination therapy is between 5% of the MTD and the MTD. In another embodiment of the invention, the dose of the benzoquinone ansamycin when used in combination therapy is between 5% of the MTD and 75% of the MTD. In another embodiment of the invention, the dose of the benzoquinone ansamycin when used in combination therapy is between 25% of the MTD and 75% of the MTD.

The dosages of the benzoquinone ansamycin and the Hsp90 client protein inhibitor when used in combination therapy may require further optimization depending upon the compounds being used, the disease or condition being treated, and the individual medical condition of the patient. Relevant factors include the activity of the specific compound employed; the age, body weight, general health, sex, and diet of the subject; the time and route of administration and the rate of excretion of the drug; and the severity of the condition being treated.

The present invention provides compositions of matter that are formulations of one or more active drugs and a pharmaceutically acceptable carrier. In one embodiment, the formulation comprises a novel benzoquinone ansamycin analog of the invention. In another embodiment, the formulation comprises a novel benzoquinone ansamycin analog of the invention as a mixture with an Hsp90 client protein inhibitor for use in combination therapy in accord with the methods of the present invention. In both of these embodiments, the active compounds may be in their free form or where appropriate as pharmaceutically acceptable derivatives such as prodrugs, esters, or salts.

The composition may be in any suitable form such as solid, semisolid, or liquid form. See Pharmaceutical Dosage Forms and Drug Delivery Systems, 5$^{th}$ edition, Lippicott Williams & Wilkins (1991), incorporated herein by reference. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

In one embodiment, the compositions containing a compound useful in the methods of the invention are Cremophore®-free. Cremophore® (BASF Aktiengesellschaft) is a polyethoxylated castor oil which is typically used as a surfactant in formulating low soluble drugs. However, because Cremophore® can case allergic reactions in a subject, compositions that minimize or eliminate Cremophore® are preferred.

Where applicable, the compounds useful in the methods of the invention may be formulated as microcapsules and nanoparticles. General protocols are described for example, by Microcapsules and Nanoparticles in Medicine and Pharmacy by Max Donbrow, ed., CRC Press (1992) and by U.S. Pat. Nos. 5,510,118; 5,534,270; and 5,662,883 which are all incorporated herein by reference. By increasing the ratio of surface area to volume, these formulations allow for the oral delivery of compounds that would not otherwise be amenable to oral delivery.

The compounds useful in the methods of the invention may also be formulated using other methods that have been previously used for low solubility drugs. For example, the compounds may form emulsions with vitamin E or a PEGylated derivative thereof as described by PCT publications WO 98/30205 and WO 00/71163, each of which is incorporated herein by reference. Typically, the compound useful in the methods of the invention is dissolved in an aqueous solution containing ethanol (preferably less than 1% w/v). Vitamin E or a PEGylated-vitamin E is added. The ethanol is then removed to form a pre-emulsion that can be formulated for intravenous or oral routes of administration. Another method involves encapsulating the compounds useful in the methods of the invention in liposomes. Methods for forming liposomes as drug delivery vehicles are well known in the art. Suitable protocols include those described by U.S. Pat. Nos. 5,683, 715; 5,415,869, and 5,424,073 which are incorporated herein by reference relating to another relatively low solubility cancer drug paclitaxel and by PCT Publication WO 01/10412 which is incorporated herein by reference relating to epothilone B. Of the various lipids that may be used, particularly preferred lipids for making encapsulated liposomes include phosphatidylcholine and polyethyleneglycol-derivitized distearyl phosphatidyl-ethanolamine.

Yet another method involves formulating the compounds useful in the methods of the invention using polymers such as polymers such as biopolymers or biocompatible (synthetic or naturally occurring) polymers. Biocompatible polymers can be categorized as biodegradable and non-biodegradable. Biodegradable polymers degrade in vivo as a function of chemical composition, method of manufacture, and implant structure. Illustrative examples of synthetic polymers include polyanhydrides, polyhydroxyacids such as polylactic acid, polyglycolic acids and copolymers thereof, polyesters polyamides polyorthoesters and some polyphosphazenes. Illustrative examples of naturally occurring polymers include proteins and polysaccharides such as collagen, hyaluronic acid, albumin, and gelatin.

Another method involves conjugating the compounds useful in the methods of the invention to a polymer that enhances aqueous solubility. Examples of suitable polymers include polyethylene glycol, poly-(d-glutamic acid), poly-(l-glutamic acid), poly-(l-glutamic acid), poly-(d-aspartic acid), poly-(l-aspartic acid), poly-(l-aspartic acid) and copolymers thereof. Polyglutamic acids having molecular weights between about 5,000 to about 100,000 are preferred, with molecular weights between about 20,000 and 80,000 being more preferred and with molecular weights between about 30,000 and 60,000 being most preferred. The polymer is conjugated via an ester linkage to one or more hydroxyls of an inventive geldanamycin using a protocol as essentially described by U.S. Pat. No. 5,977,163 which is incorporated herein by reference.

In another method, the compounds useful in the methods of the invention are conjugated to a monoclonal antibody. This method allows the targeting of the inventive compounds to specific targets. General protocols for the design and use of conjugated antibodies are described in Monoclonal Antibody-Based Therapy of Cancer by Michael L. Grossbard, ed. (1998), which is incorporated herein by reference.

The amount of active ingredient that may be combined with the carrier materials to produce a single dosage form will vary depending upon the subject treated and the particular mode of administration. For example, a formulation for intravenous use comprises an amount of the inventive compound ranging from about 1 mg/mL to about 25 mg/mL, preferably from about 5 mg/mL to 15 mg/mL, and more preferably about 10 mg/mL. Intravenous formulations are typically diluted between about 2 fold and about 30 fold with normal saline or 5% dextrose solution prior to use.

In one aspect of the present invention, the compounds useful in the methods of the invention are used to treat cancer. In one embodiment, the compounds of the present invention are used to treat cancers of the head and neck which include but are not limited to tumors of the nasal cavity, paranasal sinuses, nasopharynx, oral cavity, oropharynx, larynx, hypopharynx, salivary glands, and paragangliomas. In another embodiment, the compounds of the present invention are used to treat cancers of the liver and biliary tree, particularly hepatocellular carcinoma. In another embodiment, the compounds of the present invention are used to treat intestinal cancers, particularly colorectal cancer. In another embodiment, the compounds of the present invention are used to treat ovarian cancer. In another embodiment, the compounds of the present invention are used to treat small cell and non-small cell lung cancer. In another embodiment, the compounds of the present invention are used to treat breast cancer. In another embodiment, the compounds of the present invention are used to treat sarcomas, including fibrosarcoma, malignant fibrous histiocytoma, embryonal rhabdomysocarcoma, leiomysosarcoma, neuro-fibrosarcoma, osteosarcoma, synovial sarcoma, liposarcoma, and alveolar soft part sarcoma. In another embodiment, the compounds of the present invention are used to treat neoplasms of the central nervous systems, particularly brain cancer. In another embodiment, the compounds of the present invention are used to treat lymphomas which include Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

In another embodiment, the compounds and compositions useful in the methods of the invention are used at sub-cytotoxic levels in combination with other agents in order to achieve highly selective activity in the treatment of non-cancerous diseases. In this embodiment, the compounds useful in the methods of the invention are used to reduce the cellular levels of Hsp90 client proteins, which are then effectively inhibited by the second agent. Binding of the client proteins to Hsp90 stabilizes the client proteins and maintains them in a soluble, inactive form ready to respond to activating stimuli. Binding of a benzoquinone ansamycin analog to Hsp90 results in targeting of the client protein to the proteasome, and subsequent degradation. For systems such as the steroid receptor, however, Hsp90 forms an integral part of the functional receptor complex along with several other proteins such as Hsp70, Hsp40, p23, hip, Hsp56, and immunophilins. Hsp90 appears to regulate the activity of the steroid receptor by maintaining the receptor in a high-affinity hormone-binding conformation. Binding of geldanamycin to Hsp90 appears to result in dissociation of p23 from the complex and reduce the level of hormone binding to the receptor (Fliss et al. (2000) "Control of estrogen receptor ligand binding by Hsp90," *J. Steroid Biochem. Mol. Biol.* 75: 223-30; Kimmins and MacRae (2000), "Maturation of steroidreceptors: an example of functional cooperation among molecular chaperones and their associated proteins," *Cell Stress Chaperones* 5: 76-86.

Thus, Hsp90 inhibitors such as geldanamycin, geldanamycin analogs, radicicol, and the like can be used in accord with the methods of the present invention to alter the function of hormone receptors, making it easier to inhibit the associated signal pathways using low levels of a second drug which targets the proteins involved in those signaling pathways. Such a combination therapy can be useful to reduce non-specific toxicity associated with therapy by reducing the levels of the drugs required.

In another embodiment, the compounds useful in the methods of the invention are used to treat non-cancerous diseases or conditions characterized by undesired cellular hyperproliferation, including neurodegenerative diseases, psoriasis, stenosis, and restenosis.

In another embodiment, the compounds useful in the methods of the invention are used in combination with other agents as described above to treat non-cancerous diseases or conditions characterized by undesired cellular hyperproliferation, including neuro-degenerative diseases, psoriasis, stenosis, and restenosis. Specific examples of non-cancerous diseases treatable by this combination therapy include neurodegenerative diseases, such as Alzheimer's, Parkinson's, Huntington's and the like. There is evidence that the immunophilin FKBP-52 is involved as a client protein for Hsp90 in the formation of various steroid receptor complexes and plays a role in the regeneration of damaged neurons (Gold et al., "Immunophilin FK506-Binding Protein 52 (Not FK506-Binding Protein 12) Mediates the Neurotrophic Action of FK506," 1999, *J. Pharmacology & Exp. Ther.* 289: 1202-1210). The combination of geldanamycin, a geldanamycin analog, radicicol, or the like with a second agent which binds to and/or inhibits FKBP-52 in accord with the methods of the present invention can thus be used to treat neurodegenerative diseases.

Further examples of non-cancerous diseases treatable by the combination therapy of the present invention include non-cancerous diseases characterized by cellular hyperproliferation, such as psoriasis, stenosis, and restenosis. Cell proliferation is regulated by protein tyrosine kinases, many of which are known to be client proteins for Hsp90. Psoriasis is thought to involve the epidermal growth factor receptor (EGFR), a protein tyrosine kinase, and inhibitors of EGFR have been proposed as treatments for psoriasis (Ben-Bassat & Klein, "Inhibitors of Tyrosine Kinases in the Treatment of Psoriasis," (2000), *Curr. Pharm. Des.* 6: 933-942). Geldanamycin and herbimycin have been shown to block maturation of EGFR (Sakagami et al., "Benzoquinoid ansamycins (herbimycin A and geldanamycin) interfere with the maturation of growth factor receptor tyrosine kinases," (1999) *Cell Stress Chaperones* 4: 19-28). The combination of geldanamycin or a geldanamycin analog with an inhibitor of EGFR in accord with the methods of the present invention can thus be used to treat psoriasis.

The compounds useful in the methods of the invention may also be used to treat stenosis and restenosis, particularly associated with in vivo devices such as stents. In one embodiment, the compounds useful in the methods of the invention are used to coat stents and other surgically-implantable devices. In another embodiment, the compounds useful in the methods of the invention are used in combination with other agents as described above to coat stents, catherters, prostheses, and other in vivo devices.

A detailed description of the invention having been provided above, the following examples are given for the purpose of illustrating the present invention and shall not be construed as being a limitation on the scope of the invention or claims.

EXAMPLE 1

Preparation of
17-alkylamino-17-desmethoxygeldanamycins

The general procedure for preparing 17-alkylamino-17-desmethoxygeldanamycins is as follows. The geldanamycin analog (25 mmol) is suspended in 350 mL of anhydrous $CH_2Cl_2$ under inert atmosphere. A solution of the alkylamine (50 mmol) in 10 mL of $CH_2Cl_2$ is added dropwise. After 1 hour, the mixture is evaporated to dryness and the residue is dissolved in 50 mL of chloroform and precipitated by addition of 600 mL of hexane. Filtration and vacuum drying yields the product. The products are characterized by NMR and LC/MS. Compounds prepared according to this method include:
17-allylamino-17-desmethoxygeldanamycin;
17-(2-(dimethylamino)ethyl)amino-17-desmethoxygeldanamycin;
17-ethylamino-17-desmethoxygeldanamycin;
17-propylamino-17-desmethoxygeldanamycin;
17-butylamino-17-desmethoxygeldanamycin;
17-(cyclopropyl)methylamino-17-desmethoxygeldanamycin;
17-cyclobutylamino-17-desmethoxygeldanamycin;
17-(2-phenylcyclopropyl)amino-17-desmethoxygeldanamycin;
17-(2-fluoroethyl)amino-17-desmethoxygeldanamycin;
17-(2,2-difluoroethyl)amino-17-desmethoxygeldanamycin;
17-azetidinyl-17-desmethoxygeldanamycin;
17-amino-17-desmethoxygeldanamycin;
17-(3-(dimethylamino)propylamino-17-desmethoxygeldanamycin;
17-(4-(dimethylamino)butylamino-17-desmethoxygeldanamycin;
17-(3-dimethylamino)-2-propylamino-17-desmethoxygeldanamycin;
17-(2-dimethylamino)-1-propylamino-17-desmethoxygeldanamycin;
17-(N-ethylpyrrolidin-2-yl)methylamino-17-desmethoxygeldanamycin;
17-(1-pyrazinyl)ethylamino-17-desmethoxygeldanamycin;
17-(2-bis(2-hydroxyethyl)amino)ethylamino-17-desmethoxygeldanamycin;
17-(N-methylpyrrolidin-2-yl)ethylamino-17-desmethoxygeldanamycin;
17-(3-(diethylamino)propylamino-17-desmethoxygeldanamycin;
17-(3-(4-morpholino)propylamino-17-desmethoxygeldanamycin;
17-(4-imidazolyl)ethylamino-17-desmethoxygeldanamycin;
17-(1-methyl-4-imidazolyl)ethylamino-17-desmethoxygeldanamycin;
17-(1-methyl-5-imidazolyl)ethylamino-17-desmethoxygeldanamycin;
17-(4-pyridyl)ethylamino-17-desmethoxygeldanamycin;
17-(2-hydroxyethyl)amino-17-desmethoxygeldanamycin;
17-(1-hydroxymethyl)propylamino-17-desmethoxygeldanamycin;
17-(2-(hydroxymethyl)cyclohexyl)amino-17-desmethoxygeldanamycin;
17-(2-dioxolan-1-yl)ethylamino-17-desmethoxygeldanamycin;
17-(3,3-dimethoxypropyl)amino-17-desmethoxygeldanamycin;
17-(2-tert-butoxycarbonylamino)ethylamino-17-desmethoxygeldanamycin; and
17-(N-methyl 2-tert-butoxycarbonylamino)ethylamino-17-desmethoxygeldanamycin.

EXAMPLE 2

Preparation of 11-O-allyl-17-alkylamino-17-desmethoxygeldanamycins

The general procedure for preparing 11-O-allyl-17-alkylamino-17-desmethoxy-geldanamycins is as follows. The 17-alkylamino-17-desmethoxy-geldanamycin analog (10 mmol), allyl tert-butyl carbonate (14 mmol), palladium acetate (0.1 mmol), and triphenylphosphine (0.67 mmol) are dissolved in 60 mL of freshly distilled, air-free tetrahydrofuran under inert atmosphere. The mixture is heated at reflux for 16 hours, and is monitored by thin-layer chromatography. Upon completion, the solvents are removed in vacuo and the product isolated by silica gel chromatography.

EXAMPLE 3

Preparation of
11,17-linked-17-amino-17-desmethoxygeldanamycins

The general procedure for preparing 11,17-linked-17-amino-17-desmethoxy-geldanamycins is as follows. The 11-O-allyl-17-alkylaminogeldanamycin analog (10 mmol), and benzylidene-bis(tricyclohexylphosphine)ruthenium dichloride (5 mmol) are dissolved in 250 mL of anhydrous $CH_2Cl_2$ under inert atmosphere, and the reaction is monitored by thin-layer chromatography. After 24 hours, the reaction is concentrated and the residue is purified by silica gel chromatography.

EXAMPLE 4

Interaction of Geldanamycin Analogs and Cytotoxic Agents in SKBr3 Cells

SKBr3 and H358 cell lines were obtained from American Type Culture Collection (Manassas, Va.). Cells were maintained in McCoy'5A medium with 10% fetal bovine serum. 17-AAG and 17-DMAG were dissolved in DMSO at 10 mM and stored at −20° C.

Cells were seeded in duplicate in opaque-walled 96-well microtiter plates at 4000 cells per well and allowed to attach overnight. Serial dilutions of each drug were added, and the cells were incubated for 72 hours. The $IC_{50}$ was determined using the CellTiter-Glo Luminescent Cell Viability Assay (Promega, Madison, Wis.), which correlates with the number of live cells.

For the drug combination assay, cells were seeded in duplicate in 96-well plates (4000 cells/well). After an overnight incubation, cells were treated with drug alone or in combination. Based on the $IC_{50}$ values of each individual drug, combined drug treatment was designed at constant ratios of two drugs, i.e., equivalent to the ratio of their $IC_{50}$. Three different treatment schedules were used. The first treatment schedule used simultaneous exposure to both 17-AAG and the second cytotoxic agent for 72 hours. In the second schedule, the cells were exposed to 24 hours of 17-AAG or 17-DMAG. The second cytotoxic agent was then added to the cells and incubated for 48 hours. In the third treatment schedule, cells were exposed to the second cytotoxic agent alone for 24 hours followed by addition of 17-AAG or 17-DMAG for 48 hours. Cell viability was determined by luminescent assay (Promega). Combination analysis was performed using Calcusyn software (Biosoft, Cambridge, UK). The "combination index" (CI) refers to a measure of the additivity of the effects of two drugs administered in combination, and was calculated according to the formula:

$$CI=[D]_1/[D_x]_1+[D]_2/[D_x]_2$$

wherein $[D]_1$ and $[D]_2$ represent the concentrations of the first and second drug, respectively, that in combination provide a response of x % in the assay, and $[D_x]_1$ and $[D_x]_2$ represent the concentrations of the first and second drug, respectively, that when used alone provide a response of x % in the assay. According to this formula, a CI=1 indicates a simple additive effect of the two drugs in combination, whereas a CI<1 indicates synergism and a CI>1 indicates antagonism between the two drugs.

Addition of 17-AAG or 17-DMAG to cells after exposure to Iressa synergistically increased the cytotoxicity of Iressa (FIG. 3). An additive effect was detected when cells were exposed to 17-AAG or 17-DMAG before Iressa. Exposure of cells to 17-AAG or 17-DMAG and Iressa simultaneously also produced an additive effect. Thus the optimal synergistic effect is only observed when there is prior exposure of the cells to the protein kinase inhibitor, followed by exposure to the benzoquinone ansamycin after waiting for a period of time to allow development of efficacy of the protein kinase inhibitor.

Figure 5:
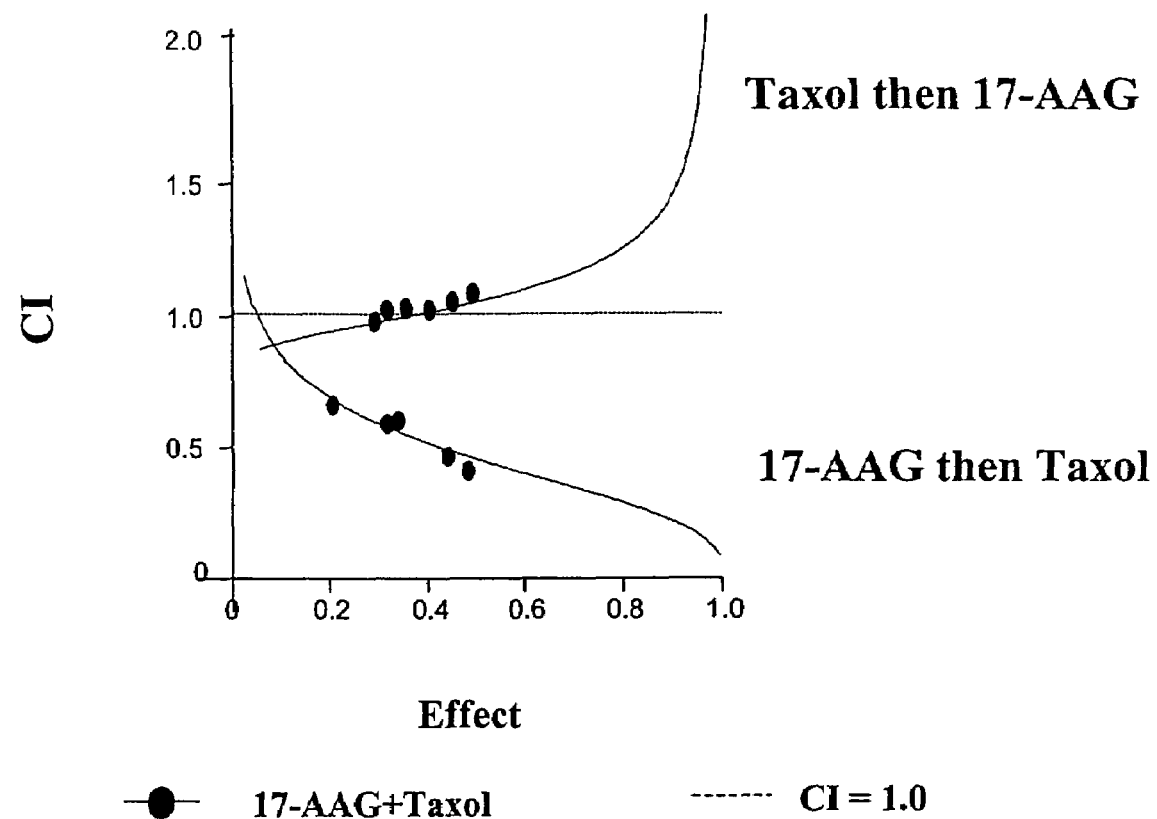
FIG. 5 shows the results of treating H358 cells with 17-AAG and the microtubule stabilizing agent paclitaxel according to the methods of the present invention.

In contrast, addition of 17-AAG or 17-DMAG to cells after exposure to paclitaxel additively increased the cytotoxicity of paclitaxel (FIG. 5). A synergistic effect was observed when cells were exposed to 17-AAG or 17-DMAG first, and later treated with paclitaxel. In this case, optimal synergism is only observed when the cells are first exposed to the benzoquinone ansamycin, followed by exposure to the microtubule stabilizing agent after waiting for a period of time to allow development of efficacy of the benzoquinone ansamycin.

EXAMPLE 5

Production of 28-desmethylgeldanamycin by AT Domain Substitution

Substitution of the acyltransferase domain in module 1 of the geldanamycin PKS gene with an AT domain specific for malonyl-CoA instead of 2-methylmalonyl-CoA results in formation of 28-desmethyl-geldanamycin. The domain substitution is created by introducing a malonyl-CoA specific acyltransferase domain from a heterologous PKS gene, for example from the rapamycin, tylosin, or FK520 PKS genes or the like, into the geldanamycin PKS locus by homologous recombination into a geldanamycin producing strain, aided by a selectable antibiotic resistance gene, then isolating the recombinants resulting from double crossover events in which the wild-type acyltransferase domain is replaced with one specific for malonyl-CoA. The AT domain of module 1 is encoded by nucleotides 1626 through 2670, approximately, of SEQ ID NO:1. This sequence information together with the methods described in U.S. Pat. Nos. 6,399,789; 6,403,775; and 5,962,290 allows one skilled in the art to construct recombination vectors that result in replacement of the native AT domain of module 1 with an AT domain having a specificity for malonyl-CoA. Suitable examples of AT domains with specificity for malonyl-CoA may be found in the rapamycin PKS genes (modules 2, 5, 8, 9, 11, 12, and 14), as described in U.S. Pat. No. 6,399,789, as well as the tylosin PKS genes (modules 3 and 7) as described in U.S. Pat. No. 5,876,991; the spiramycin genes (modules 1-3 and 7), as described in U.S. Pat. No. 5,945,320; the FK520 genes (modules 3 and 10), as described in WO 00/20601; the pikromycin genes (module 2) as described in WO 99/61599; the narbomycin genes (module 2), as described in U.S. Pat. No. 6,303,767; the avermectin genes (module 2), and others. Each of the above documents is incorporated herein by reference. Fermentation of a host cell comprising the resulting hybrid PKS together with the remaining geldanamycin biosynthetic genes under conditions wherein the native strain produces geldanamycin, followed by extraction of the broth and purification provides 28-desmethyl-geldanamycin.

EXAMPLE 6

Production of 28-desmethylgeldanamycin by Site-directed Mutagenesis

The acyltransferase domain in module 1 of the geldanamycin PKS gene is mutagenized according to the methods described in Reeves et al., "Alteration of the substrate specificity of a modular polyketide synthase acyltransferase domain through site-directed mutagenesis," *Biochemistry* 2001, 40: 15464-15470, and in U.S. patent application Ser. No. 60/310,730, entitled "Alteration of the substrate specificity of a modular PKS AT domain," which is incorporated herein by reference. The amino acid sequence Tyr-Ala-Ser-His (SEQ ID NO: 3), encoded by nucleotide sequence TAC-GCC-TCC-CAC (SEQ ID NO: 4) at positions 2194 to 2205 in SEQ ID NO:1, is mutagenized using methods known to one skilled in the art to generate the mutant amino acid sequence His-Ala-Phe-His (SEQ ID NO: 5), for example by mutagenesis of the nucleotide sequence to CAC-GCC-TTC-CAC (SEQ ID NO: 6) as described in the Reeves et al. reference cited above. Fermentation of a host cell comprising the resulting mutagenized PKS together with the remaining geldanamycin biosynthetic genes under conditions wherein the native strain produces geldanamycin, followed by extraction of the broth and purification provides 28-desmethyl-geldanamycin.

EXAMPLE 7

Production of 4,5-dihydro-5-hydroxygeldanamycin by Reductive Domain Swap

The coding sequence for the reduction cassette of module 6, which has both DH and KR domains, is replaced with a coding sequence for a reduction cassette that has only a KR domain. The reduction cassette is contained in the sequence between the end of the AT domain, at approximately nucleotide position 2805 of SEQ ID NO:2, and the beginning of the ACP domain, at approximately nucleotide position 6028 of SEQ ID NO:2. This sequence information together with the methods described in U.S. Pat. Nos. 6,399,789; 6,403,775; and 5,962,290 allows one skilled in the art to construct recombination vectors that result in replacement of the native reduction cassette of module 6 with a cassette encoding only a KR domain. Suitable examples of cassettes encoding only a KR domain may be found in the erythromycin and rapamycin PKS genes, as described in U.S. Pat. No. 6,399,789. Fermentation of a host cell comprising the resulting hybrid PKS together with the remaining geldanamycin biosynthetic genes under conditions wherein the native strain produces geldanamycin, followed by extraction of the broth and purification provides 4,5-dihydro-5-hydroxy-geldanamycin.

EXAMPLE 8

Production of 4,5-dihydro-5-hydroxygeldanamycin by Site-directed Mutagenesis

Inactivation of the dehydratase domain in module 6 of the geldanamycin PKS gene by site-specific mutation of the wild-type domain results in production of 4,5-dihydro-5-hydroxygeldanamycin. The DH domain of module 6 is encoded by nucleotides 2805 to 4276, approximately, of SEQ ID NO:2. Two particular sequences may be targeted for mutational inactivation of the DH domain. In one embodiment, the DNA sequence encoding the DH peptide motif His-Val-Ile-Ser-Gly-Ala-Val-Leu-Val-Pro (SEQ ID NO: 7), nucleotides 2956 through 2985 of SEQ ID NO:2, is mutated so as to produce a peptide having an amino acid other than histidine at the first position. The CAC codon encoding histidine is mutated, for example to CAA or CAG to encode a glutamine, as illustrated in SEQ ID NO: 8. Fermentation of a host cell comprising the resulting mutagenized PKS together with the remaining geldanamycin biosynthetic genes under conditions wherein the native strain produces geldanamycin, followed by extraction of the broth and purification provides 4,5-dihydro-5-hydroxy-geldanamycin.

EXAMPLE 9

Production of 4,5-dihydro-5-hydroxygeldanamycin by Deletion

A portion of the nucleotide sequence in module 6 between the end of the AT domain (approximately nucleotide 2805 of SEQ ID NO:2) and the start of the KR domain (approximately nucleotide 5212 of SEQ ID NO:2) is deleted to provide a modified PKS for production of 4,5-dihydro-5-hydroxy-geldanamycin. The nucleotide sequence between 2805 and 3270, approximately, of SEQ ID NO:2 is deleted so as to leave a linker region between the AT and KR domains of approximately 465 amino acids. Fermentation of a host cell comprising the resulting modified PKS together with the remaining geldanamycin biosynthetic genes under conditions wherein the native strain produces geldanamycin, followed by extraction of the broth and purification provides 4,5-dihydro-5-hydroxy-geldanamycin.

EXAMPLE 10

Production of 15-hydroxygeldanamycin by Reductive Domain Swap

The reduction cassette in module 1 is encoded by the sequence between the end of the AT domain, at approximately nucleotide position 2670 of SEQ ID NO:1, and the beginning of the ACP domain, at approximately nucleotide position 5895 of SEQ ID NO:1. This sequence information together with the methods described in U.S. Pat. Nos. 6,399,789; 6,403,775; and 5,962,290 allows one skilled in the art to construct recombination vectors that result in replacement of the native reduction cassette of module 1 with a cassette encoding only a KR domain. Suitable examples of cassettes encoding only a KR domain may be found in the erythromycin and rapamycin PKS genes, as described in U.S. Pat. No. 6,399,789. Fermentation of a host cell comprising the resulting hybrid PKS together with the remaining geldanamycin biosynthetic genes under conditions wherein the native strain produces geldanamycin, followed by extraction of the broth and purification provides 15-hydroxy-geldanamycin.

EXAMPLE 11

Production of 15-hydroxygeldanamycin by Site-directed Mutagenesis

Inactivation of the dehydratase domain in module 1 of the geldanamycin PKS gene by site-specific mutation of the wild-type domain results in production of 15-hydroxygeldanamycin. The DH domain of module 1 is encoded by nucleotides 2670 to 4140, approximately, of SEQ ID NO:1. Two particular sequences may be targeted for mutational inactivation of the DH domain. In one embodiment, the DNA sequence encoding the DH peptide motif His-Ala-Val-Ser-Gly-Thr-Val-Leu-Leu-Pro (SEQ ID NO: 9), nucleotides 2821 through 2850 of SEQ ID NO:1, is mutated so as to produce a peptide having an amino acid other than histidine at the first position. The CAC codon encoding histidine is mutated, for example to CAA or CAG to encode a glutamine as illustrated in SEQ ID NO:10. Fermentation of a host cell comprising the resulting mutagenized PKS together with the remaining geldanamycin biosynthetic genes under conditions wherein the native strain produces geldanamycin, followed by extraction of the broth and purification provides 15-hydroxygeldanamycin.

EXAMPLE 12

8,9-epoxy-8,9-dihydrogeldanamycin

To a solution of geldanamycin (120 mg, 0.21 mmol) in dichloromethane (5 mL) was added 85% 3-chloroperoxybenzoic acid (93 mg, 0.42 mmol). After the mixture was stirred at room temperature overnight, TLC showed the reaction to be complete. The reaction mixture was diluted with ethyl acetate and washed subsequently with aqueous sodium sulfite, aqueous bicarbonate, and brine. The organic solution was dried over anhydrous sodium sulfate, filtered, and evaporated to dryness. The crude product was purified by flash chromatography on silica gel, giving 30 mg of 8,9-epoxy-8,9-dihydrogeldanamycin as a yellow solid. The compound was characterized by NMR and MS spectrometry.

EXAMPLE 13

8,9-epoxy-17-[2-(dimethylamino)ethylamino]-8,9-dihydro-17-demethyoxygeldanamycin To a solution of 8,9-epoxy-8,9-dihydrogeldanamycin (20 mg, 0.035 mmol) in 1,2-dichloroethane (2 mL) was added N,N-dimethylethylenediamine (10 μL, 0.09 mmol). The mixture was stirred at room temperature overnight. The reaction was worked up by diluting with ethyl acetate and washing sequentially with aqueous bicarbonate and brine. The organic solution was dried over anhydrous sodium sulfate, filtered, and evaporated to dryness. The crude product was purified by HPLC on a C-18 column, giving 10 mg of 8,9-epoxy-17-[2-(dimethylamino)ethylamino]-8,9-dihydro-17-demethyoxygeldanamycin as a purple solid. The compound was characterized by NMR and MS spectrometry.

EXAMPLE 14

17-[2-(dimethylamino)ethylamino]-17-demethyoxygeldanamycin

To a solution of geldanamycin (60 mg, 0.1 mmol) in 1,2-dichloroethane (4 mL) was added N,N-dimethylethylenediamine (22 μL, 0.2 mmol). The mixture was stirred at room temperature overnight. The reaction was diluted with ethyl acetate and washed sequentially with aqueous bicarbonate and brine. The organic solution was dried over anhydrous sodium sulfate, filtered, and evaporated to dryness. The crude product was purified by flash chromatography on silica gel, giving 59 mg of 17-[2-(dimethylamino)-ethylamino]-17-demethyoxygeldanamycin as a purple solid.

The compound was characterized by NMR and MS spectrometry.

EXAMPLE 15

17-[2-(dimethylamino)ethylamino]-11-oxo-17-demethyoxygeldanamycin

To a solution of 17-[2-(dimethylamino)ethylamino]-17-demethyoxygeldanamycin (50 mg, 0.08 mmol) in chloroform (5 ml) was added the Dess-Martin periodinane (208 mg, 0.49 mmol). The mixture was heated to reflux for one hour. The reaction mixture was diluted in ethyl acetate and washed subsequently with aqueous sodium thiosulfate, aqueous bicarbonate, and brine. The organic solution was dried over anhydrous sodium sulfate, filtered, and evaporated to dryness. The crude product was purified by HPLC on a C-18 column, giving 26 mg of 17-[2-(dimethylamino)ethylamino]-11-oxo-17-demethyoxygeldanamycin as a purple solid.

The compound was characterized by NMR and MS spectrometry.

EXAMPLE 16

17-[2-(dimethylamino)ethylamino]-11-oxo-17-demethyoxygeldanamycin-11-oxime

To a solution of 17-[2-(dimethylamino)ethylamino]-11-oxo-17-demethyoxy-geldanamycin (30 mg, 0.049 mmol) in ethanol (4 mL) was added triethylamine (60 μL, 0.43 mmol) and hydroxylamine hydrochloride (30 mg, 0.4 mmol). After the mixture was stirred at room temperature for 3 h, TLC showed reaction complete. After ethanol was evaporated, the residue was dissolved in chloroform and water. The organic layer was dried over anhydrous sodium sulfate, filtered, and evaporated to dryness. The crude product was purified by flash chromatography on silica gel, giving 10 mg of 17-[2-(dimethylamino)ethylamino]-11-oxo-17-demethyoxygeldanamycin-11-oxime as a purple solid. The compound was characterized by NMR and MS spectrometry.

---

What is claimed is:

1. A method for treatment of breast cancer or lung cancer in a subject suffering therefrom, comprising the steps of:
   (a) administering to said subject a substantially sub-toxic dose of an Hsp90 client protein inhibitor, wherein the Hsp90 client protein inhibitor is N-(3-chloro-4-fluorophenyl)-7-methoxy-6-[3-(4-morpholinyl(propoxy]-4-quinazolinamine (Iressa);
   (b) waiting a period of time sufficient to allow development of a substantially efficacious response; and
   (c) administering to said subject a synergistic dose of a benzoquinone ansamycin, wherein the benzoquinone ansamycin is 17-allylamino-17-desmethoxy-geldanamycin (17-AAG) or 17-(2-dimethylamino)ethylamino-17-desmethoxygeldanamycin (17-DMAG).

2. A method for treatment of breast cancer or lung cancer in a subject suffering therefrom, comprising the steps of:
   (a) administering to said subject a synergistic dose of a benzoquinone ansamycin, wherein the benzoquinone ansamycin is 17-allylamino-17-desmethoxy-geldanamycin (17-AAG) or 17-(2-dimethylamino)ethylamino-17-desmethoxygeldanamycin (17-DMAG);
   (b) waiting a period of time sufficient to allow development of a substantially efficacious response; and
   (c) administering to said subject a sub-toxic dose of an Hsp90 client protein inhibitor, wherein the Hsp90 client protein inhibitor is paclitaxel.

3. The method of claim 1, wherein the benzoquinone ansamycin is 17-(2-dimethylamino)ethylamino-17-desmethoxygeldanamycin (17-DMAG).

4. The method of claim 1, wherein the benzoquinone ansamycin is 17-allylamino-17-desmethoxy-geldanamycin (17-AAG).

5. The method of claim 2, wherein the benzoquinone ansamycin is 17-(2-dimethylamino)ethylamino-17-desmethoxygeldanamycin (17-DMAG).

6. The method of claim 2, wherein the benzoquinone ansamycin is 17-allylamino-17-desmethoxy-geldanamycin (17-AAG).

* * * * *

SEQUENCE LISTING

<160> NUMBER OF SEQ ID NOS: 10

<210> SEQ ID NO 1
<211> LENGTH: 6210
<212> TYPE: DNA
<213> ORGANISM: Streptomyces geldanus

<400> SEQUENCE: 1

```
tccgacgagc cggtggcgat cgtggcgatg ggctgccacc tgccgggcga ggtcgcgacg      60
cccgaggacc tgtggcggtt ggtggccgac gggcgggacg cgatcgccgg gttcccggag     120
gaccggggct gggacctggc cgggctcttc gactccgacc cggacgccgt gggcaagtcc     180
```

-continued

```
tatgtgcgcg agggcggttt cctcaccgac gcgggcggat tcgacgccgc attcttcggc    240
atctcgcccc gtgaggcgct ggcgatggac ccgcagcagc ggttgctgct ggagaccgcg    300
tgggagacct tcgagaatgc cggaatcgac ccgggttcgc tgcacggcac cgacgtcggt    360
gtgttcagcg gagtgatgta ccacgattac ggggccgacg ccgggacggc ggcggagggc    420
ctggagggc atctcggcgt gggcagcgcg gggagcgtcg tctccgggcg ggtggcctac    480
gcgctgggcc tgaccgggcc cgcggtgacc gtggacaccc cctgctcgtc ctccctggta    540
gcgctgcacc tggcggttca ggcggtgcgc acgggcgaat gctcgctggc gctcgccggg    600
ggtgtcgcgg tgatgagcag gccgacgtcg ttcatcgagt tctcccgcca gcgtggcctc    660
gcccccgacg ccgctgcaa gtccttcgcg gagggcgccg acggcaccaa ctggtccgag    720
ggtgtcgggt tggtgttgct ggagcggctg tccgatgccc ccgcaatgg gcatgaggtg    780
ctcgccgtcg tccgtggcac cgccgtgaac caggacggcg ccagcaacgg cctgaccgcg    840
cccaacggcc cgtcccagga acgggtgatc cggcaggcgc tggcgaacgc cgggctgacg    900
gtggccgatg tggacgcggt cgaggcccac ggcacgggca cgagtctcgg cgacccgatc    960
gaggcccagg cactcctggc cacctacggg caggagcggc cggaggatca gccgctgtgg   1020
ctggggtcgt tgaagtcgaa catcgggcat gcgcaggcgg cggcgggcgc ggccggtgtc   1080
atcaagatgg tccaggccat gcggcacggc gtactgccca aaaccctcca cgccgacgag   1140
cccaccagca aggtcgactg gacgtcaggt gcggtgtcgc tactgtccga ggcccggccc   1200
tggccggaga cgggacaccc ccgccgcgcc ggaatctcct ccttcggcgt cagcgggacg   1260
aacgcacacg tggtcctgga acaggcaccc ctggaagcgg ctgcacccga acacaggcg   1320
agcgacgcgg gcgctcctgg gctcgtggcc acgggcggcg tagtgccgtg ggtgctgtcc   1380
gccaagactc ctgcggcgct cgcgctcag gcagagcgtc tggtcagcca tctggagtcc   1440
gggagcgacg ccaacccggt cgatgtgggc tggtcgctgg ccaccaccg gcggcgttg   1500
gagcaccgcg cggtcatcct ggcgacggat gccgaaggag gcatggcgac ggcgcgggct   1560
ctggcggagg ggcggcctga cccgctcctg gtcaccggac agaccggaac agacggcaaa   1620
accgtgttca tcttccccgg ccaaggcgcc caatgggtgg gcatgggagc ccaactcctc   1680
aacacctcac ccgtcttcgc cgcccgcctg cgtgagtgcg ccgatgctct agcgccgtat   1740
accgactggt cgctcatcga cgtcatcacc ggcacgccg acgctccctc gcttgagcgt   1800
gtcgacgtcg tacagcccgc caccttcgcc gtcgtcgtct ccctcgccgc actctggcaa   1860
tccgtgggca tccaccccga cgccgtcatc ggccactccc aaggcgaaat cgccgccgcc   1920
tgcgtcgccg acacctcac cctcaccaac gccgccaaaa tcgtcaccct ccgcagccag   1980
accatcgccc accctcgc cggacacggc ggcatgatgt ccctcgccac cccgccgac   2040
accatcgacc tcaccaactg gcacggcaaa ctctggatcg ccgcacacaa cagccccaac   2100
gccaccgtca tcgcaggcga caccgacgcc ctgcaccaac tccacacccca ctacaccgac   2160
cagggcacca gagcccgcat catccccgtc gactacgcct cccacaccgg acacgtcgac   2220
accatcaaaa accagctaca agacgtactc gacggcatca ccctcgaacc cggcaccatc   2280
ccctggctct ccaccgtcac cggacagtgg atcgaaccca caccgtcgg cgacagctac   2340
tggtaccgca acctccgcca aaccgtgcaa ttcgagcaca ccatccacac cctcgccgac   2400
cagggctacc gcacctacat cgaaatcagc ccccaccccg tcctcaccac cgccatccaa   2460
gaaaccctcg aagccaacga caccccccaac accaccatcg tcaccggcac cctccgccgc   2520
gacgacgaca ccccccacccg cctcctcacc aacctcgccc acctcaccac caacggaaca   2580
```

```
ccagtcaact ggcccaccct cttcacaggc acccaaccca cccgcatccc cctccccacc    2640
taccccttcc aacaccacca ctactggctc ccccgcaaca ccagcgcagg cgatgtgagt    2700
gccgtgggcc tccagggcac gggccacccg ctggccgggg ccgtggtgag cgtgcccgac    2760
accgggggtg tgctgctcac cgggcagttg tcggtggcca cccacccgtg gctggccgac    2820
cacgccgtct ccggaacggt gctgctgccg ggcaccgcga tggccgaact cgccatccgc    2880
gccggagacg agaccgacac ccccaccctg gaagagctgg tcatcggcca gccgatgaca    2940
ctgcccgaag acggtgcact acatgtccag gtactggtcg gcggcgtgga ggacgggcgc    3000
cgaggggtgc ggatctactc tcgccccgac gcggcccagg aacaggaatg gctggagcac    3060
gcctcgggca cactcgccac gcagccggac ggttcggccg agggcggcat ggagaacggc    3120
atgcccgagt ggccgccgcc cggtgtcgag ccgatcgctc tggatgactt ctacgacgac    3180
ctcgcccagg ccgggtatga gtacgggccc gccttccgcg ggctgaaggc ggtctggaag    3240
cgcgatggcg aggtgttcgc ggaggccgcg ctgccggagg agcagacgga cgtcgccggc    3300
cggttcggta tccatccggc gctgctggac gccgcgttgc acgcgagcaa cttctgtgtg    3360
cccccggccc cgggccaaac gctcctcccc ttcgtgtgga acggcgtacg gctgctggcg    3420
gcgggagcca cggccgtccg tgtgcgcgcc cgcgccaccg gcacggactc gttcacgatc    3480
agcctgttcg acagcaccgg ctcccccgtc gcctcggtgg actccctggt gctccgggcg    3540
atcagtcccg agcagctcgc tgccgcctcc ggcggtgccg gtcggtccgc tgatgcgctg    3600
ttcacgctga ctggaccgga gcaccccacc ggcctgggga ccgaggtttc ctgggccacc    3660
ctcggcgatg cccacaccga cgtggacgcc cacgtggacg cgctcatcgc gggagaggac    3720
cggcccgggg ccgtggtcgc cgacaccgcg gcctgggccg ccggggacac cggcctgccc    3780
gcgcgggccc gggatctggc cgcccgcgcg ctggacctgg tgcagcggtg gtcggccga    3840
cccgaactcg ccgacgtccg gctcgtgttg ctcactcgtg gggcggtgtc cgtgcacgac    3900
accgccgagg tcaccgaccc ggccgccgcc gcgatctggg gcctggtccg ctccgcccag    3960
tccgaacacc cgggccggat cgccctggtg gacaccgacg acgtgtcgcg ggaggcgctg    4020
cccgaggcgg tggcggccgg cgagccgcaa gtggcgctgc gccgtgggct gctgtgggtg    4080
cctcgtctgt gcggtcgcc gcagggtctc gccgtacccg cgcacgagca ctggtacctc    4140
gacgtctcgg agaagggcag cctggagaac ctggtgctgc ggccggatcc ggaggccacc    4200
gcgccgctgg ccaccggtca ggtccggatc gaggtccgcg ccgccggtca gaacttccgg    4260
gacgtactcg tcgcgctcgg cggcgtggcg ggtcaggagg gtctgggcgg cgagggtgcc    4320
gggggtggtga ccgaggtcgg gcccgggtc gagggcctgg cggtgggcga ccgggtgatg    4380
ggcctgttcc cgcgctcgtt cggcccgctg gccatcgcgg acgcgcgcac ggtcgcgccg    4440
atccccgagg gctggtcgta cgccacggcc gccggggtgc cggtggccta tctgacggca    4500
ctgtacgggc tgcgggacct gggcaccgta cagccgggtg agacggtgct ggtgcacgcc    4560
gccgcgggcg gtgtgggcat ggccgccgtc cagttggcgc ggcacttcgg cgccaccgtg    4620
tacgccaccg cccacccgtc gaagcaccat gtgctgaccg cgctgggggt gccggagggg    4680
catctggcgt ccagccgcga cctcggtttc gcctcggcgt ttcccgcgct ggatgtggtg    4740
ctgaactccc tcaccggcga gtatgtggac gcctcgctgg gctgctcgg cacgggtggc    4800
cgtttcgtgg agatgggcaa gaacgacatc cgcgatcccg cctcggtcgc cgcagcacat    4860
cccggtgtgg gctatcaggc gttcgacctg ggaggtgacg cgggccctga ccggatccgg    4920
```

-continued

```
gagctgctcg cggagctggt ggaactgttc gaggcgggcc ggatcgagcc gcttccgata    4980
cggcactggg acgtcaccca ggcgccgacg gccttccggt ggatgagcca ggggcggcac    5040
accggcaaga tcgtgctcac cctcccccga gccctggacc cggacggcac cgtcctgatc    5100
accggtggca ccggaaccct cggcgccacc atcgcccgcc acgtcgtcac ccaccacggc    5160
gcgcgccagt tgctcctcat cagccgtcag ggtcccgacg cccccggcgc caccgatctc    5220
accaccgaac tcaccgaact cggcgccacc gtccgcatca ccgcctgcga caccgccgac    5280
cgcgaccaac tcgccgcgct cctcgccgac atccccgccg cccaccccct caccgccgtc    5340
atccacaccg ccggcgccct ggacgacggt gtcctgaccg cgctcacccc ggaccgcctc    5400
gacaccgtct ccgccccaa ggtcgacgcc gtcacccacc tccacgacct cacccgcgac    5460
caggacctgg ccgcgttcgt catctactcg tccgccgccg aacgctcgg caacgcgggg    5520 caggccaact acgccgccgc caatgccttc ctcgacgcct cgcccagtg gcggcacgcc    5580 cgccaccggc ccgccacttc gctggcgtgg gggctgtgga gcgacaccag cacgctcacc    5640
tcgacgatgg acgccaccga cgtacgccgc acacggcggg cgggggtgct gggcatggac    5700
aacgccgagg cgctgcgggt gttcgacacc gggttgcggt ccgggcggcc cgcgctggtg    5760
gccgcgaaga tcgacctcac cgccctgcgc gcgccggacg ccgagttgtc gccgctgctg    5820
cgcggactgg cccgtccggc gcgccgcacc gcgcgcaccg cggccccggc ggccggtggt    5880
ctgtcggggc agctggccgg gctgtccccc gccgggcagc gggagttcct gctcaacctg    5940 gtgcgggcg aggccgcggt ggtcctcgcc cacgccggtc ctgaggcgat cgagccgacc    6000
gtggcgttca aggagatggg tttcgactcg ctgacggcgg tcgaactgcg caaccggctg    6060
aatgcggcga ccgggctgcg gctccccgcc acgttgctct tcgaccaccc gactccggct    6120
cttctcaccg agctgttcca taccgagttg gcggcggcc cggcacccgc cgcggcggcc    6180
ccggtgaccg tgcgtgccgc cgctgacgag                                    6210
```

<210> SEQ ID NO 2
<211> LENGTH: 6360
<212> TYPE: DNA
<213> ORGANISM: Streptomyces geldanus

<400> SEQUENCE: 2

```
atggctgcgt cccgggaaga cctggtcaag gcgctgcgta cctcgctgat ggacgccgag      60
cggctgaagc gggagaacga ccggctgatc gccgagtcca ccgaaccggt ggcgatcgtg     120
gcgatggcgt gccggctgcc gggtgggtg accgacccgg agtcgctgtg ggagctggtg      180
gacgaggggc gggacgcgat cgggccgttc cccacggatc gcggctggga cctggagacc     240
ctgttcgact ccgatccgga cgccgtgggc aagtcctacg tacgcgaggc gggttcctg     300 gaggggggcg gcggattcga cgccgccttc ttcggcatct cgccgcgcga ggccctgtcg     360
ctggacccgc agcagcggct gctgctggag accgcgtggg agaccttcga gcgggcgggg     420
atggatccgc ggtcggtgga gggccgggac atcgcggtgt cgccgggggg cagcggccag     480
gggtacggcg gcgtccgggg tgaggcgccc aagggcctgg agggctatct gggggtcggc     540
gcttccggca gtgtcatctc cgggcgcgtg tcgtacacgc tcgggctgac cggtcccgcc     600
gtgaccgtga acaccgcctg ctcgtcctcg ctggtggccg cccatctcgc cgtgcaggcg     660
ctgcggtccg gcgaatgttc catggcgctg gccggtggtg tcgccgtgat gggccagccc     720
accgccttcg tcgagttctc ccggcagcgt ggcctggcgc ccgacgggcg ctgcaagtcc     780
ttcggcgcgg gcgccgacgg caccaccctg gtccgaaggtg tcgggctcgt tctgctggag     840
```

-continued

```
cggctgtcgg acgcccgccg caacggccac gaagtgctgg ccgtgatccg gggcaccgcg      900
gtcaaccagg acggcgcctc caacggactc accgcgccca acggcccctc ccaggagcgg      960
gtgatccgcc aggccctgtc caacgccggg ctgacggtgg ccgacgtgga cgccgtcgag     1020
gcccacggca ccggcaccgc cctcggcgac cccatcgaag cccaggccgt tctcgccacc     1080
tacggccaaa gccgcccgga gggcggccg ctgtggctcg gctccctcaa gtccaacatc      1140
ggccacgcgc aggccgcagc gggcatcgcc agtgtcatca agaccgtcat ggccttacgc     1200
cacgccggt tgccgaagac cctccacgcc gaacagccca cctcccaggt gaactggacg      1260
tcgggcgcgg tgtccctgct cgccgaggcg cgggcgtggc cggagaccgg acacgcccgc     1320
cgcgccggga tctcctcctt cggcgtcagc gggacgaacg cacacgtcat cctggaacag     1380
gcccctgagg aagccgaggc gaccggggag aacaccgccg atcaggaacc gcccgtacgc     1440
tcggcggagt ccgccgaccc cggcccggtc gccaccggcc acgtggtgcc gtggctgctc     1500
tcgggccata cgcaggaggc gctgcgtgcc caggccgccc ggctgctgac ccaggtgcgc     1560
gagacgccct ccgacagtcc gcgggacgtg ggctggtcac tggccaccac ccggacccgg     1620
ctggaccacc gcgcggtcgt actgtgcgcc gatgccgagc aggccgtcgc ggggctggag     1680
gcggtggcct cgggcacgtc cgcccggtcg gcggtcaccg ggtccgtggc ctccggaaag     1740
gtggcggtgc tgttcaccgg gcagggcagc cagcgggccg gaatgggccg cgaactgcac     1800
ggcgcccacc cggtgttcgc gcgggccttc gacgccgtgt cgcccagtt cggcgacctg     1860
cgcgacgggg acgacaaggt ctcgctggcc gaggtgatct tcgccgagga ggggtcggcg     1920
acggcagcgc tgctggaccg gaccgagttc acccagcccg cgctgttcgc gctggaggtg     1980
gcgctgttcc ggctcgtgga gtcgtgggga gtgcgcccg cgtatgtgct gggccactcg      2040
atcggcgaag tggcggcggc ccatgtggcc ggggtcctgt ccctgccgga cgcctgcaca     2100
ttggtgcggg cgcgcgggcg gctgatgcag caactcaccg cgaccggggc gatggtcgcg     2160
gtggaggcgg ccgaggacga ggtggcgccg ctgctcgcgg ggaaggagca caaggtctcc     2220
atcgccgcg tcaacggccc ggcctccgtg gtcgtctccg gtgacgagga cgtggtcacg      2280
gcggtggcgg agacgctggc gcggcagggc cgcaagacca agcggctcgt ggtctcgcac     2340
gccttccact ccccccacat ggacgggatg ctggacgcgt tccgcgaggt ggcgtcgcgg     2400
ctggcctacg cgccaccccg gatacccgtg gtgtcgaacc tcaccggcgc ggtcgccgat     2460
cccgaggagc tgtgctcccc cgagtactgg gtacggcatg cacgtggcgc ggtgcggttc     2520
ctcgacggtg tccgcacact ggccgacgag ggcgtgcgca cccatctgga actcggcccg     2580
gatgggtgc tgaccgcgat ggggcaggac tgtctgcccg aggcggacgc ggcgttcgtg      2640
ccgtccctgc gtccgggcgt ccaggagccg cacgcggtgc tggccgggct cgccggcctg     2700
tacgtacggg gtgtgcgggt ggactgggac gcgatgttcg ccgggtccgg cgcccggccc     2760
gtcgcccttc ccacgtacgc cttccagcac gagcactact ggctggagcg ggccgccggc     2820
tccggcgacg tggcgcggt ggggctcggc gaggcgggcc atccgctgct gggcgcggtg      2880
gtgcagctcc cggagacggg cggggtgcag ctcagcgggc ggctgtcggt acgggcccag     2940
ccctggctgg gcgaacacgt catctccggg gcggtgctgg tgcccggcac cgccatggtg     3000
gaactggccg tccgcgccgg ggacgagacc ggcaccccg tgctggagga ctggtgatc      3060
gggcagccga tggtgctgcc cggcgacacc gccctcagtg tccaggtcgt cgtgggcgcg     3120
gacgagggcg gcggcgtac ggtgcggatc tactcccgta ccgacggggg caccgactgg      3180
```

```
accgagcacg ccaccggcac gctcgcggcg cagggcccgg caccgctgga cggggccgcg   3240
ggcggggccg ccgtcgagtg gccgcccgcg gaagccgagc cgatccccgt ggaggacttc   3300
taccgctcgc tcgtcgacgc cggatacgcg tacggaccgg cgttccgcgg gctcgtcgcc   3360
gcgtggcgcc gggacggtga gatcttcggc gatgtggcgc tgccggaggc gtccgtcgcg   3420
gaggccgagc ggttcggcat ccacccggcg ctgctggacg ccgcactgca cgcgggcagc   3480
ttctgtctgc cctccgaccc ggcgcgacag gtgaccctgc tgccgttcgc ctggaacacc   3540
gtgcgtctgc acgcgggcgg cgcgtccgcg gtccgggtgc atgtccgccc ggtcggcgac   3600
gacgccttct cggtacgcct gaccgacggc tcgggccaga cggtggcctc ggtggactcg   3660
ctcaccttgc gggcggtgga cccggcccag ctcaagatcg gcacggccga cgacgcgctg   3720
tggacggtcc gctggagcga gacctcgctg ccggacggcg cggtctcctg gccccgctc    3780
ggcgagtcgg ccaccggggc aaccgggggc tacgcgccca caggggacgg cggaggccca   3840
gggggcgcgc ttcccgacgt cctcgtggcc gatacgcgcg cctgggccga agacctcacc   3900
ggaccgccga ccgcgcgggc ccgggagctc accggccgcc tgctggagga gatccagcgg   3960
tgggtcgccg acgacgccat ggccgggacg cggctcgccg tggtcacccg cggcgcggtc   4020
gcggtccacg acgacaccga ggtcaccgac ccggccgcca ccgcgctctg ggcctggtc    4080
cgctcggccc aggccgaaca cccggggcgg gtggccctgg tggatgccga cggagcgtgc   4140
gaggaactgc ccgccggggt gtggtccggg gacgagcccc aactggcggt gcgcggtggc   4200
gccgtgtggg tgccacgcct cacccgggtc gagcccggcc tgcgcgtgcc cgcgcaggcg   4260
tcgtggcatc tggactcggc cgagtacggc accctggaca atctggcgct gctgcccgac   4320
gaggccgagc ccgcaccgcc ggcggccggt caggtgcgga tcgaggtccg cgccgccggg   4380
ctcaacttcc gggatgtcct ggtggctctc ggcatgtatc cgggccggtc ggtgatcggc   4440
acggagggcg ccggtgtggt gaccgaagtc ggtccgggcg tcacgggcct ggccgtgggc   4500
gaccgggtga tgggcctgtt ctccggctcg ttcggaccgc tggccaccgc cgacgcgcgc   4560
acggtgatcc ggatgccgga gggctggtcg ttcggcacgg cggccggggt gccggtggcc   4620
tatctgacgg cgctgtacgc gttgcaggac ctcggggagg tccagccggg cgagacggtc   4680
ctggtgcacg ccgccgcggg cggtgtgggc atggccgccg tccagctcgc acagcacttc   4740
ggcgccaccg tcctgggcac cgcccacccc tccaagcacc acgcactcca ccggctgggc   4800
gttcccgccg aacggctcgc ctccagccgc gacctcgcct acgccgacac cttccccacc   4860
gccgacgtcg tcctcaactc cctcaccggc gagcacatcg acgcctccct cggacttctc   4920
aaccccggcg gccggttcct ggagatgggg aagaccgacc tgcgggagcc cggcgaggtc   4980
ggggcgcggc atccggaggt cacctaccgg gcgttcgatc tcggtgggga ggccccgcg    5040
gagcgggtgc gggagttgct gcaccagttg gtggagctgt cgaggcggg ccggatcgag    5100
ccgctgccgg tacggcagtg ggacatcacc cgcgcccccg aggcgttccg ctggatgagt   5160
caggggcggc ataccggcaa gatcgtgctc accctgccac gcgccctgga cccggacggc   5220
accgtcctgt tcaccggtgg cacgggcacc ctcggcgcca cgatcgcccg ccacttctc    5280
acccagcacg gcgcacgcca tctgctgctg gtcagccgcc ggggaccgga cgcacctggc   5340
gccacagacc tgaccaccga actcaccgaa ctcggcgcca ccgtccgcat caccgcctgc   5400
gacaccgccg accgcgacca actcgccgcg ctcctcgccg acatccccgc cgaccacccc   5460
ctcaccgccg tggtccacac ggccgggacc ctcgacgacg tgtcctgac  cgcgctcacc    5520
ccggaccgcc tcgacaccgt cttccgcccc aaggtcgacg ccgtcaccca tctccacgac   5580
```

```
ctcacccgcg accacgacct ggcggcgttc gtggtgtact cgtccgccgc cggagtcctc    5640
ggcgggcccg gccagggcaa ctactccgcc gccaacgcct atctggacgg actcgcacag    5700
tggcggcgtg cgcacgggct ccccgccacc tcgctggcgt ggggcatgtg ggcgcagacc    5760
agtggcatga cggccgggct cggctccggc gatctgcacc gggtgcggcg tggcggcatc    5820
gtcgggctgt ccacggcgga ggccctggac ctgttcgacc ggtcggtggc gtccgggctg    5880
tccctgctgg tgccgttgcg gttggacatc gccgccctcg gtgcggaggc cgcggaaccg    5940
ccgccgctgc tgcggggtct ggtccggccg gccggcgta cggcccggcc ggtgccgaag    6000
gccggtgagg gcggcctcgc cgaacggctg gccgggctgt cggcggccga acaggagcgt    6060
ctgctcatcg agttgatccg cgaacaggcc gcttcggtgc tcgggttccc cacggtcgac    6120
ccgatcgggc cggagcaggc gttccgcgac atggggttcg actcgctgac cgcggtggag    6180
ctgcgcaacc gcctcaacac ggccaccggg ctacggctcc ccgcaacgct ggtcttcgac    6240
cacccgagcc ccttggccac cgccgagttc ctgcgggatc aactgggcgg gcgcgcggtc    6300
gaggcggcgc ccgcccggc ccggcgtgac cggtcggctc cggacggggc cgaggatccg    6360
```

<210> SEQ ID NO 3
<211> LENGTH: 4
<212> TYPE: PRT
<213> ORGANISM: Artificial Sequence
<220> FEATURE:
<223> OTHER INFORMATION: Specificity peptide sequence od module 1 AT
      domain

<400> SEQUENCE: 3

Tyr Ala Ser His
 1

<210> SEQ ID NO 4
<211> LENGTH: 12
<212> TYPE: DNA
<213> ORGANISM: Artificial Sequence
<220> FEATURE:
<223> OTHER INFORMATION: Specificity nucleotide sequence of module 1 AT
      domain

<400> SEQUENCE: 4
tacgcctccc ac                                                          12

<210> SEQ ID NO 5
<211> LENGTH: 4
<212> TYPE: PRT
<213> ORGANISM: Artificial Sequence
<220> FEATURE:
<223> OTHER INFORMATION: Specificity peptide sequence of module 1 AT
      domain

<400> SEQUENCE: 5

His Ala Phe His
 1

<210> SEQ ID NO 6
<211> LENGTH: 12
<212> TYPE: DNA
<213> ORGANISM: Artificial Sequence
<220> FEATURE:
<223> OTHER INFORMATION: Specificity nucleotide sequence of module 1 AT
      domain

<400> SEQUENCE: 6

```
cacgccttcc ac                                                    12

<210> SEQ ID NO 7
<211> LENGTH: 10
<212> TYPE: PRT
<213> ORGANISM: Artificial Sequence
<220> FEATURE:
<223> OTHER INFORMATION: Signature peptide sequence of module 6 DH
      domain

<400> SEQUENCE: 7

His Val Ile Ser Gly Ala Val Leu Val Pro
 1               5                  10

<210> SEQ ID NO 8
<211> LENGTH: 30
<212> TYPE: DNA
<213> ORGANISM: Artificial Sequence
<220> FEATURE:
<223> OTHER INFORMATION: Signature nucleotide sequence of module d DH
      domain

<400> SEQUENCE: 8
cacgtcatct ccggggcggt gctggtgccc                                  30

<210> SEQ ID NO 9
<211> LENGTH: 10
<212> TYPE: PRT
<213> ORGANISM: Artificial Sequence
<220> FEATURE:
<223> OTHER INFORMATION: Signature peptide sequence of module 6 DH
      domain

<400> SEQUENCE: 9

His Ala Val Ser Gly Thr Val Leu Leu Pro
 1               5                  10

<210> SEQ ID NO 10
<211> LENGTH: 30
<212> TYPE: DNA
<213> ORGANISM: Artificial Sequence
<220> FEATURE:
<223> OTHER INFORMATION: Signature nucleotide sequence of module 6 DH
      domain

<400> SEQUENCE: 10
cacgccgtct ccggaacggt gctgctgccg                                  30
```